United States Patent [19]

Bodary et al.

[11] Patent Number: 5,726,290
[45] Date of Patent: Mar. 10, 1998

[54] SOLUBLE ANALOGUES OF INTEGRINS

[75] Inventors: Sarah C. Bodary; Cornelia M. Gorman; John W. McLean, all of San Francisco; Mary A. Napier, Hillsborough, all of Calif.

[73] Assignee: Genentech, Inc., South San Francisco, Calif.

[21] Appl. No.: 445,042

[22] Filed: May 19, 1995

Related U.S. Application Data

[62] Division of Ser. No. 380,227, Jan. 30, 1995, abandoned, which is a continuation of Ser. No. 218,878, Mar. 28, 1994, abandoned, which is a continuation of Ser. No. 821,337, Jan. 13, 1992, abandoned, which is a continuation of Ser. No. 444,490, Dec. 1, 1989, abandoned, which is a continuation-in-part of Ser. No. 290,224, Dec. 22, 1988, abandoned.

[51] Int. Cl.$^6$ .................. C07K 14/705; C07K 19/00
[52] U.S. Cl. .................. 530/350; 530/387.3
[58] Field of Search .................. 530/350, 387.3

[56] References Cited

U.S. PATENT DOCUMENTS

| 4,761,371 | 8/1988 | Bell et al. | 435/69.1 |
|---|---|---|---|
| 5,498,600 | 3/1996 | Murray et al. | 514/12 |

FOREIGN PATENT DOCUMENTS

| 139416 | 5/1985 | European Pat. Off. |
|---|---|---|
| 244221 | 11/1987 | European Pat. Off. |
| 244267 | 11/1987 | European Pat. Off. |
| 278776 | 8/1988 | European Pat. Off. |
| WO 89/00200 | 1/1989 | WIPO |
| WO 91/19511 | 12/1991 | WIPO |

OTHER PUBLICATIONS

Argraves et al., "Amino Acid Sequence of the Human Fibronectin Receptor" *Journal of Cell Biology* 105:1183–1190 (Sep. 1987).

Argraves et al., "cDNA Sequences from the α subunit of the fibronectin receptor predict a transmembrane domain and a short cytoplasmic peptide" *Journal of Biological Chemistry* 261(28):12922–12924 (Oct. 5, 1986).

Arnaout et al., "Expression of a soluble and functional form of the human B2 integrin CD11b/CD18" *Journal of Cell Biology* 111(5):768 (1990).

Arnaout, A. M., et al., "Amino acid sequence of the alpha subunit of human leukocyte adhesion receptor mol complement receptor type 3" *Journal of Cell Biology* 106:2153–2158 (1988).

Bennett et al., "Expression of Human Platelet Glycoprotein IIb in Cult. Mamm. Cells." *61st Scientific Sessions 1234* (1988).

Berman et al., "Biosynthesis and Function of Membrane Bound and Secreted Forms of Recombinant CD11b/CD18 (Mac–1)" *J. Cell. Biochem.* 52:183–195 (1993).

Bodary et al., "Expressioin of recombinant platelet glycoprotein IIbIIIa results in a functional fibrinogen–binding complex" *Journal of Biological Chemistry* 264(32):18859–18862 (1989).

Boulianne, G. L. et al., "Production of functional chimaeric mouse/human antibody" *Nature* 312(5995):643–646 (Dec. 1984).

Bray et al., "Physical linkage of the genes for platelet membrane glycoproteins IIb and IIIa" *Proc. Natl. Acad. Sci. USA* 85:8683–8687 (Nov. 1988).

Bray et al., "Platelet Glycoprotein IIb" *J. Clin. Invest.* 80:1812–1817 (Dec. 1987).

Buck and Horwitz, "Cell Surface Receptors for extracellular matrix molecules" *Ann. Rev. Cell Biol.* 3:179–205 (1987).

Chothia, "Principles that Determine the Structure of Proteins" *Annual Review of Biochem.* 53:537–572 (1984).

Cierniewski et al., "Palmitylation of the glycoprotein IIb–IIIa complex in human blood platelets" *Journal of Biological Chemistry* 264(21):12158–12164 (1989).

Corbi et al., "cDNA cloning and complete primary structure of the α subunit of a leukocyte adhesion glycoprotein" *EMBO Journal* 6(13):4023–4028 (1987).

Corbi et al., "The human leukocyte adhesion glycoprotein mac–1 (complement receptor type 3, CD11b) α subunit" *Journal of Biological Chemistry* 263(25):12403–12411 (1988).

Cosgrove et al., "A genomic clone encoding the α chain of the OKM1, LFA–1, and platelet glycoprotein IIb–IIIa molecules" *Proc. Natl. Acad. Sci. USA* 83:752–756 (1986).

Devlin et al., "Alteration of amino–terminal codons of human granulocyte–colony–stimulating factor increases expression levels and allows efficient processing by methionine aminopeptidase in *Escherichia coli*" *Gene* 65:13–22 (1988).

Doyle et al., "Analysis of progressive deletions of the transmembrane and cytoplasmic domains of influenza hemagglutinin" *Journal of Cell Biology* 103:1193–1204 (1986).

Doyle et al., "Mutations in the cytoplasmic domain of the influenza virus hemagglutinin affect different stages of intracellular transport" *Journal of Cell Biology* 100:704–714 (1985).

Early et al., "Two mRNAs can be produced from a single immunoglobulin µ Gene by alternative RNA processing pathways" *Cell* 20:313–319 (1980).

Falkner and Zachau, "Expression of mouse immunoglobulin genes in monkey cells" *Nature* 298:286–288 (1982).

(List continued on next page.)

*Primary Examiner*—John Ulm
*Assistant Examiner*—Karen E. Brown
*Attorney, Agent, or Firm*—Wendy M. Lee; Deirdre L. Conley

[57] ABSTRACT

Methods are provided for the preparation in recombinant host cells of biologically active soluble variants of discretely encoded, heteromultimer polypeptide receptors. Such variants are synthesized by the secretion from recombinant transformants of transmembrane-modified heteromultimer receptors. Preferred receptors are extracellular matrix, cell surface, or plasma protein-binding receptors such as GPIIb-IIIa.

14 Claims, 14 Drawing Sheets

OTHER PUBLICATIONS

Fisher et al., "HIV infection is blocked in vitro by recombinant soluble CD4" *Nature* 331:76–86 (1988).

Fitzgerald et al., "Comparison of cDNA-derived protein sequences of the human fibronectin and vitronectin receptor α-subunits and platelet glycoprotein IIb" *Biochemistry* 26:8158–8165 (1987).

Fitzgerald et al., "Protein Sequence of Endothelial Glycoprotein IIIa Derived from a cDNA Clone" *Journal of Biological Chemistry* 262:3936–3939 (1987).

Garoff, Henry, "Using recombinant DNA techniques to study protein targeting in the eucaryotic cell" *Ann. Rev. Cell Biol.* 1:403–445 (1985).

Gascoigne et al., "Secretion of a chimeric T-cell receptor-immunoglobulin protein" *Proc. Natl. Acad. Sci. USA* 84:2936–2940 (1987).

Gething & Sambrook, "Cell-surface expression of influenza haemagglutinin from a cloned DNA copy of the RNA gene" *Nature* 293:620–625 (1981).

Gething and Sambrook, "Construction of influenza hemagglutinin genes that code for intracellular and secreted forms of the protein" *Nature* 300:598–603 (1982).

Gething et al., "Expression of wild-type and mutant forms of influenza hemagglutinin: the role of folding in intracellular transport" *Cell* 46:939–950 (1986).

Gething et al., "Mutational analysis of the structure and function of the influenza virus hemagglutinin" *Current Topics in Membranes and Transport*, Academic Press, Chapter 2, vol. 23:17–41 (1985).

Ginsberg et al., "Cytoadhesins, integrins, and platelets" *Thromb. Haemost.* 59(1):1–6 (1988).

Groux et al., "Suppressor effects and cyclic AMP accumulation by the CD29 molecule of CD4+ lymphocytes" *Nature* 339:152–154 (1989).

Heidenreich et al., "Organization of the gene for platelet glycoprotein IIb" *Biochemistry* 29:1232–1244 (1990).

Hibbs et al., "The Cytoplasmic Domain of LFA–1 B subunit: sites required for binding . . . " *Journal of Experimental Medicine* 174:1227–1238 (Nov. 1991).

Holzmann et al., "Identification of a Murine Peyer's Patch-specific lymphocyte homing receptor as an integrin molecule with an α chain homologous to human VLA–4α" Cell 56:37–46 (1989).

Hurtley and Helenius, "Protein oligomerization in the endoplasmic reticulum" *Ann. Rev. Cell Biol.* 5:277–307 (1989).

Hynes, RO, "Integrins: A Family of Cell Surface Receptors" *Cell* 48:549–554 (1987).

Johnson et al., "Properties of the Insulin Receptor Ectodomain" *Proc. Natl. Acad. Sci. USA* 85:7516–7520 (1988).

Karnik et al., "Structure-function studies on bacteriorhodopsin" *Journal of Biological Chemistry* 262(19):9255–9263 (1987).

Kishimoto et al., "Cloning of the β Subunit of the Leukocyte Adhesion Proteins: Homology to an Extracellular Matrix Receptor Defines a Novel Supergene Family" *Cell* 48:681–690 (1987).

Kishimoto et al., "Leukocyte Adhesion Molecules" *Springer-Verlag* (Springer et al., ed.) p. 15.

Kohler, G., "Immunoglobulin chain loss in hybridoma lines" *Proc. Natl. Acad. Sci. USA* 77(4):2197–2199 (1980).

Kozak, M., "At least six nucleotides preceding the AUG initiator codon enhance translation in mammalian cells" *J. Mol. Biol.* 196:947–950 (1987).

Krangel et al., "Characterization of B Lymphoblastoid Cell Line Mutant that Secretes HLA–A2" *J. Immunol.* 132(6):2984–2991 (1984).

Larson et al., "Cloning of the alpha subunit of human LFA–1" *J. Cell. Biochem.* S11D:272 (1987).

Larson et al., "Primary structure of the leukocyte function–associated molecule–1 α subunit: an integrin with an embedded domain defining a protein superfamily" *Journal of Cell Biology* 108:703–712 (1989).

Loeb and Drickamer, "The chicken receptor for endocytosis of glycoproteins contains a cluster of N–acetylglucosamine–binding sites" *Journal of Biological Chemistry* 262(7):3022–3029 (1987).

Loftus et al., "Molecular cloning and chemical synthesis of a region of platelet glycoprotein IIb involved in adhesive function" *Proc. Natl. Acad. Sci. USA* 84:7114–7118 (1987).

MacKrell et al., "The lethal myospheroid gene of Drosophila encodes a membrane protein homologous to vertebrate integrin B subunits" *Proc. Natl. Acad. Sci. USA* 85:2633–2637 (Apr. 1988).

Mariuzza and Winter, "Secretion of a homodimeric VαCk T–cell receptor–immunoglobulin chimeric protein" *Journal of Biological Chemistry* 264(13):7310–7316 (1989).

Munro, "Uses of chimaeric antibodies" *Nature* 312:597 (1984).

Neuberger et al., "Recombinant antibodies possessing novel effector functions" *Nature* 312(5995):604–608 (Dec. 1984).

O'Toole et al, "Efficient surface expression of platelet GPI-Ib–IIIa Requires both subunits" *Blood* 74(1):14–18 (1989).

Owen and Lamb, "The T cell antigen receptor" *Immune Recognition* (IRL Press) pp. 37–42 (1988).

Phillips et al., "The Platelet Membrane Glycoprotein IIb–IIIa Complex" *Blood* 71(4):831–843 (1988).

Phillips et al., "The Platelet Membrane Glycoprotein IIb/IIIa Complex" *Annals N.Y. Acad. Sci.* 509:177–187 (1987).

Poncz et al., "Structure of the Platelet Membrane Glycoproteiin IIb" *Journal of Biological Chemistry* 262(18):8476–8482 (Jun. 25, 1987).

Rogers et al., "Gene segments encoding transmembrane carboxyl termini of immunoglobulin gamma chains" *Cell* 26:19–27 (1981).

Rogers et al., "Two mRNAs can be produced from a single immunoglobulin λ gene by alternative RNA processing pathways" *Cell* 20:303–312 (1980).

Rosa et al., "Cloning of Glycoprotein IIIa cDNA from human erythroleukemia cells and localization of the gene to chromosome 17" *Blood* 72(2):593–600 (Aug. 1988).

Rose and Bergmann, "Expression from Cloned cDNA of Cell–Surface Secreted Forms of the Glycoprotein of Vesicular Stomatitis Virus in Eucaryotic Cells" *Cell* 30:753–762 (1982).

Rose and Doms, "Regulation of protein export from the endoplasmic reticulum" *Ann. Rev. Cell Biol.* 4:257–288 (1988).

Rouslahti et al., "New perspectives in cell adhesion: RGD and Integrins" *Science* 238:491–497 (1987).

Rupp et al., "Identical VB T–cell receptor genes used in alloreactive cytotoxic and antigen plus I–A specific helpter T cells" *Nature* 315:425–427 (1985).

Sharon et al., "Expression of a $V_h C_k$ Chimaeric Protein in Mouse Myeloma Cells" *Nature* 309:364–367 (1984).

Smith et al., "Blocking of HIV–1 Infectivity by a Soluble, Secreted Form of the CD4 Antigen" *Science* 238:1704–1707 (1987).

Suzuki and Naitoh, "Amino acid sequence of a novel integriin B4 subunit and primary expression of the mRNA in epithelial cells" *EMBO Journal* 9(3):757–763 (1990).

Suzuki et al., "Amino acid sequence of the vitronectin receptor α subunit and comparative expression of adhesion receptor mRNAs*" *Journal of Biological Chemistry* 262(29):14080–14085 (Oct. 15, 1987).

Sveda et al., "Influenza virus hemagglutinin containing an altered hydrophobic carBobxy terminus accumulates intracellularly" *Journal of Virology* 49(1):223–228 (1984).

Tamkun et al., "Structure of Integrin, a Glycoprotein Involved in the Transmembrane Linkage between Fibronectin and Actin" *Cell* 46:271–282 (1986).

Thiagarajan et al., "A human erythroleukemia cell line synthesizes a functionally active glycoprotein IIb–IIIa complex capable of binding fibrinogen" *Biochimica et Biophysica Acta* 924:127–134 (1987).

Traunecker et al., "Soluble CD4 molecules neutralize human immunodeficiency virus" *Nature* 331:84–86 (1988).

Van Driel et al., "Self-association of the low density lipoprotein receptor mediated by the cytoplasmic domain" *Journal of Biological Chemistry* 262(33):16127–16134 (1987).

Wills et al., "Mutations of the Rous Sarcoma Virus env Gene that affect the transport and subcellular location of the glycoprotein products" *Journal of Cell Biology* 99:2011–2023 (1984).

Yuan et al., "Cloning and sequence analysis of a novel β 2-related integrin transcript from T lymphocytes: homology of integrin cysteine-rich repeats to domain III of laminin B chains" *Int–Immunol* (published erratum appears in Int Immunol 1991 Dec; 3(12):1373–4) 2(11):1097–1108 (1990).

Zimrin et al., "Structure of Platelet of Glycoprotein IIIa" *J. Clin. Invest.* 81:1470–1475 (May 1988).

```
                                          sau3AI
                                          mboI
                                          dpnI                                                      bsp1286
              haeIII              taqI    xhoI  alwI                                                nlaIV   banI      aluI
      rsaI    eaeI        rsaI                                                                                                      
      scaI tagI
801 CCAGAGTACTTCGACGGCTACTCGGTGGCCGTGGGCGAGTTCGACGGGATCTCAACACTACAGAATATGTCGTCGGTGCCCCACTTGGA
      GGTCTCATGAAGCTGCCGATGAGCCACCGGACCCCATGAGCCACCCGCTCAAGCTGCCCGTCAAGTTGTGATGTCTTATACAGCCACCGGGGGGTGAACCT
228    P   E   Y   F   D   G   Y   W   J   Y   S   V   A   V   G   E   F   D   G   D   L   N   T   T   E   Y   V   V   G   A   P   T   W   S
      scrFI                                                         hinPI
      bstNI                                                         thaI
                                                                    bstUI
                                                                    hinPI
                                              fnu4HI                hhaI                            hgaI
                                              bbvI                  bssHII                          ahaII         bsmI alwNI
      sau96I                    hinfI    alwNI  sfaNI bbvI hhaI                                                                 
      nlaIV
      avaII
901 GCTGGACCCTGGGAGCGGTGGAAATTTTGGATTCCTACTACCGGCTGCATCCGGCTGCGCGCAGAGCAGATGGCCTGTCTATTTTGGGCATTCAGTGGC
      CGACCCTGGGACCCTCGCCACCTTTAAAACCTAAGGATGATGGCCGACGTAGCCGACGCGCGTCTCGTCTACCGGACATAAAACCCGTAAGTCACCG
262    W   T   L   G   A   V   E   I   L   D   S   Y   Y   Q   R   L   H   R   L   R   A   E   Q   M   A   S   Y   F   G   H   S   V   A
                                                                                      scrFI
              hincII        sau3AI                                                    ncII
              ahaII         mboI                  hinPI                               mspI         haeIII
                            nlaIII                hhaI                                hpaII        eaeI
              aatII   foki mnII dpnI          haeII
1001 TGTCACTGACGTCAACGGGATGGAGGCATGATCTGCTGGTGGGCGCTCCACTGTATATGGAGAGCCGGCAGACCGAAAACTGGCCGAAGTGGGGCGT
      ACAGTGACTGCAGTTGCCCTACCTCCGTACTAGACGACCACCCGCGAGGTGACATATACCTCTCGGCCGTCTGGCTTTGACCGGCTTCACCCCCCA
295    V   T   D   V   N   G   D   G   R   H   D   L   L   V   G   A   P   L   Y   M   E   S   R   A   D   R   K   L   A   E   V   G   R
                      sau96I
                      nlaIV
                      ecoO109I    hinPI
              fnu4HI mnII         hhaI
              bbvI bstUI          thaI           bsp1286
      psti fnu4HI   pflMI         bstUI   banI   nlaIV                mnlI         aluI           hinfI
1101 GTGTATTTGTTCCTGCAGCCGCGAGCCCCACGGCCCCTGGGTGCCCCAGCGCTCCTGCTGACTGGCACAGCTCTATGGGCGATTCGGCTTCGCCATCG
      CACATAAACAAGGACGTCGGCGCTCGGGGTGCCGGGGACCCACGGGGTCGCGAGGACGACTGACCGTGTCGAGATACCCGCTAAGCCGAAGCGGTAGC
328    V   Y   L   F   L   Q   P   R   G   P   H   A   L   G   A   P   S   L   L   T   G   T   Q   L   Y   G   R   F   G   S   A   I   A
```

Fig.1(d)

```
                    scrFI
                    nciI
                    mspI                                                                    haeIII
          scrFI                                                                             sau96I
          bstNI                                            sau96I                           scrFI                              scrFI
          mnlI    taqI  foki              fnu4HI          nlaIV        ppuMI  haeIII pflMI  nciI                               bstNI
                                          bbvI   alwNI   avaII        nlaIV  eaeI   nlaIV  mspI  hpaII
1201 CACCCCTGGGCGACCTCGACCGGGATGGCTACAATGACATTGCAGTTGAGTGCTGCCCCCTACGGGGCTCCCAGTGGCCGGGGCCCAAGTGCTGGTGTTCTGGG
     GTGGGGACCCGCTGGAGCTGGCCCTACCGATGTTACTGTAACGTCAACTCACGACGGGGATGCCCCGAGGGTCACCGGCCCGGTTCACGACCACAAGGACCC
 362  P   L   G   D   L   D   R   D   G   Y   N   D   I   A   V   A   A   P   Y   G   G   P   S   G   R   G   Q   V   L   V   F   L   G
                                          sau96I
                                          avaII ppuMI
                                          eco0109I
                                          scrFI
                                          pflMI  scrFI
                                                  bstNI
                         mnlI                                                                                                              taqI
               mnlI      ddeI                           alwNI                                                       banI               taqI accI claI
1301 TCAGAGTGAGGGGCTGAGTCGAGGTCAGTCCCCTCCCCACAGGCTCTGCCTTGGCTCTCCTTCCCTTGGCTTCCCTTCCTGAGGGTGCCGTAGACATC
     AGTCTCACTCCCCGACTCAGCTCCAGTCAGGGAGGGGTGTCCGGAGACGGAACGAAGAGGAAGGGAAGGGAAGGACGAAGAAGGGAAGGAGGACTCTGTAG
 395  Q   S   E   G   L   R   S   R   P   S   Q   V   L   D   S   P   F   P   T   G   S   A   F   G   F   S   L   R   G   A   V   D   I ddeI
                                                                                               espI
                                                                                               aluI
                                             bstXI                      sacI
                                             haeIII                     hgIAI                                       mnlI      aluI
                                             sau96I scrFI               bsp1286                                     haeIII    alwNI
                 sau3AI                                                                                             stuI      pflMI
                 mboI            aluI nlaIV bstNI     rsaI banII        hphI haeI
                 dpnI            mboII                                                                              fnu4HI
1401 GATGACAACGGATACCCAGAACCTGATCGTGGGAGCTTACGGGCCAACCAGTGGCTGTGTACAGAGTCTCAGCGAGCTGAAGGCCTCCTGTCCAGCTAC
     CTACTGTTGCCTATGGGTCTTGGACTAGCACCCCTCGAATGCCCCGGTTGGTCACCGACACATGTCTCAGAGTCGCTCGACTTCCGGAGACAGGTCGATG
 428  D   D   N   G   Y   P   D   L   I   V   G   A   Y   G   A   N   Q   V   A   V   Y   R   A   Q   P   V   V   K   A   S   V   Q   L   L hinfI  hinfI              aluI        ddeI            mnlI                                    fnu4HI
                           mboII                                                                          bbvI  aluI  foki                 nlaIV
1501 TGGTGCAAGATTCACTGAATCCTGCTGTGTGAAGAGTCCTACCTGCTGTTCTCAGATCCAAGACACCCGTGAGCTGCTTCAACATCCAGATGTGTTGGAGCCAC
     ACCACGTTCTAAGTGACTTAGGACGACACACTTCTCAGGATGGACGACAAGAGTCTAGGTTCTGTGGGCACTCGACGAAGTTGTAGTCTACACACCTCGGTG
 462  V   Q   D   S   L   N   P   A   V   K   S   C   V   L   P   Q   T   K   T   P   V   S   C   F   N   I   Q   M   C   V   G   A   T
```

Fig.1(e)

```
                                                          naeI
                                                          haeIII
                                                          sau96I
                                 fnu4HI
                                 bbvI sau96I              scrFI
                                 pstI avaII               bstNI mspI      fnu4HI
                    ddeI         fnu4HI                        hpaII      bbvI fnu4HI bsp1286
     bsp1286        mnlI alui    bbvI aluI pvuII mspI    bstNI mspI       bbvI      bsp1286 banII
1601 TGGGACACAACATTCCTCAGAAGCTATCCCTAAATGCCGAGTCGACCTGGACAGAAGCCCGCCGGGTGCTGCTGCTGGGCTCTCAA
     ACCCGTGTGTTAAGGAGTCTTCGATAGGGATTTACGCCTCAGCTGGACCTGTCTTCGGGCGGCCCACGACGACGACCCGAGAGTT
495  G   H   N   I   P   Q   K   L   S   L   N   A   E   L   Q   L   D   R   Q   K   P   R   Q   G   R   R   V   L   L   G   S   Q sau3AI
               mboI
               dpnI
               xhoII
                                                                     haeIII
                   alwI                                              haeI
                   scrFI                                             nlaIII
                                                                     styI
          nlaIV                                                      ncoI
          banI        bstNI                                                         tagI  mnlI
1701 CAGGAGGCACCACCCTGAACTGGATCTGGGCGGAAAGCACAGCCCATCTGCCACCACCATGGCCTTCCTTCGAGATGAGGCAGACTTCCGGGACA
     GTCCTCCGTGGTGGGACTTGACCTAGACCCGCCTTTCGTGTCGGGTAGACGGTGGTGGTACCGGAAGGAAGCTCTACTCCGTCTGAAGGCCCTGT
528  Q   A   G   T   T   L   N   L   D   L   G   K   H   S   P   I   C   H   T   T   M   A   F   L   R   D   E   A   D   F   R   D   K sau96I
        bsp1286                                                               nlaIV
        banII                                               mnlI              haeIII        fnu4HI
        ddeI   ddeI                                                                         bbvI      nlaIII
        aluI   espI
               hgiAI
               bsp1286 mnlI
1801 AGCTGAGCCCATTGTGCTCAGCTGAAATGTGTCCCTACCGCCTGCTGTCATGAGACACCCATGTGCAGGA
     TCGACTCGGGTAACACGAGTCGACTTTACACAGGGATGGCGGACGACAGTACCTCTGTGGTACACGTCCT
562  L   S   P   I   V   L   S   L   N   V   S   L   P   P   T   E   A   G   M   A   P   A   V   V   L   H   G   D   T   H   V   Q   E nlaIV
                        scrFI                            bsp1286
        hinfI bstNI     mboII                            banII
                                                         aluI aluI
1901 GCAGACACGAATCGTCCTGGACTGTGGGGAAGATGACGTATGTGTGCCCAGCTTCACTGCCAGCGTGACGGCTCCCCGCTCTAGTTGGGCA
     CGTCTGTGCTTAGCAGGACCTGACACCCCTTCTACTGCATACACACGGGTCGAAGTGACGGTCGCACTGCCGAGGGGCGAGATCAACCCGT
595  Q   T   R   I   V   L   D   C   G   E   D   D   V   C   V   P   Q   L   Q   L   T   A   S   V   T   G   S   P   L   L   V   G   A
```

```
                                                                      scrFI
                                          sau96I                      bstNI
                                          nlaIV
                                          avaII              aluI     sau96I
                                    ppuMI                    sacI bstXI haeIII
                             aluI   ecoO109I        hgiAI    hgiAI
           fnu4HI            pvuII               bsp1286     bsp1286
           bbvI mboII hphI mnlI aluI                banII      banII                           nlaIV
2401 TGGCAGCAGAAGAAGGTGAGAGGAGCAGAAACAGCTTGACAGTCGGGACCCAAAGTGGAGCACACCTATGAGCTCCACAACAATGGCCTGGGACTGT
     ACCGTCGTCTTCTTCCACTCTCCCTCGTCTTGTCGAACTGTCAGCCCTGGGTTTCACCTCGTGTGGATACTCGAGGTGTTGTTACCGGACCCTGACA
 762  A  A  E  E  G  E  R  E  Q  N  S  L  D  S  W  G  P  K  V  E  H  T  Y  E  L  H  N  N  G  P  G  T  V scrFI                                       scrFI
                         ncII                                        haeIII
                         mspI                                        bstNI sau96I
              hphI       hpaII                     scrFI                                   ecoO109I
              ddeI  foKI                           bstNI                        sau96I
        mboII mnlI sfaNI             mnlI  bspMI   foKI                         haeIII
                                                                                mspI
                                                                                hpaII
                                                                                scrFI
                                                                                ncII
2501 GAATGGTCTTCACCTGCAGCATCCAGCTCCCGGGACAGTCCCAGCCCTCCGACCTGCTCTACATCCTGGATATACAGCCCCAGGGGGGCCTTCAGTGCTTC
     CTTACCAGAAGTGGACGTCGTAGGTCGAGGGCCCTGTCAGGGTCGGGAGGCTGGACGAGATGTAGGACCTATATGTCGGGGTCCCCCCGGAAGTCACGAAG
 795  N  G  L  H  L  S  I  H  L  P  G  Q  S  Q  P  S  D  L  L  Y  I  L  D  I  Q  P  Q  G  G  L  Q  C  F sau3AI
                                                                                         mboI
                                                                                         dpnI
                                                           hinPI                         xhoI
                   fnu4HI                                  nlaIV             sau3AI
                   bbvI foKI       mnlI          hphI      narI              mboI
            mnlI hincII                                                      dpnI         bglII
                                                                             alwI
2601 CCACAGCCCTCGTCAACCCTCTCAAGGTGGACTGGGGCTGCCTCCCCAGCCCTCCCCATTCACCCGGCCCATCACAAGCGGGATCGCAGACAGA
     GGTGTCGGGAGCAGTTGGGAGAGTTCCACCTGACCCCGACGGAGGGGTCGGGAGGGGTAAGTGGGCCGGGTAGTGTTCGCCCTAGCGTCTGTCT
 828  P  Q  P  P  V  N  P  L  K  V  D  W  G  L  P  I  P  S  P  I  H  P  A  H  H  K  R  D  R  R  Q  I haeII
                                 saval                                banI
                       bsp1286   bglI mnlI         bamHI              ahaII             pstI
           mboII       banII  fnu4HI taqI          alwI               fnuHI             bspMI
                                                              bbvI pleI
                                                         aluI hinfI hhaI rsaI
2701 TCTTCCTGCCAGAGCCCGAGAGCTCGGGCTCGAGGCTTCAGGATCACAGTTCTCGAGGTCGACGCTGCTAAGCTGCGACTCGGCCGCCCTCTAAGTCGATCAGTGTGGTGCAGTGTGACCTGCAGGA
     AGAAGGACGGTCTCGGGCTCTCGAGCCCGAGCTCCGAAGTCCTAGTGTCAAGAGCTCCAGCTGCGACGATTCGACGCTGAGCCGGCGGGAGATTCAGCTAGTCACACCTGGACGTCCT
 862  F  L  P  E  P  E  Q  P  S  R  L  Q  D  P  V  L  V  S  C  D  S  A  P  C  T  V  V  Q  C  D  L  Q  E
```

Fig.1(h)

```
                                                                        mnlI
                                                                        haeIII   sau3AI
                                                                        stuI     mboI
                                                                        haeI     dpnI        pstI
                                               haeIII       fnu4HI      mnlI     alwI        fnu4HI
         bstUI                                 haeI         bbvI                             bbvI
         hinPI         nlaIII
         hhaI          styI
         thaI          ncoI
     bstUI             haeIII
     hinPI  fnu4HI     sau96I
     hhaI   bbvI
     bssHII
2801 GATGGCGCGGGGCAGGCCATGGTGGGCCCCGTCGCCGTCGCCCTGTGCCTGGCCTTCCTGTGGCTGCCCAGCCTCTACCAGAGGCCTCTGGATCAGTTTGTGCTGCAGTCGCAC
     CTACCGCGCCCCGTCCGGTACCACCCGGGGCAGCGGCAGCGGGACACGGACCGGAAGGACACCGACGGGTCGGAGATGGTCTCCGGAGACCTAGTCAAACACGACGTCAGCGTG
 895 M  A  R  G  Q  R  A  M  V  T  V  L  A  F  L  W  L  P  S  L  Y  Q  R  P  L  D  Q  F  V  L  Q  S  H haeIII
                                                                                          sau96I
                                                                                          scrFI
                                                            mnlI                          nciI styI
                                  bsp1286                                                 fnu4HI mspI
                                  nlaIV           ddeI                                    bbvI   hpaII
                                         banI     espI   avaI  aluI                       aluI   pvuII           mnlI
         nlaIII   mnlI                            ddeI                                                                mnlI
2901 GCATGGTTCAACGTGTCCTCCCTCCCCTATGCGGTGCCCCCTGCCCGGCTCAGCCTGGGGAAGCTCAGGTGTGGACACAGCTGCTCCGGGCCTTGGAGG
     CGTACCAAGTTGCACAGGAGGGAGGGGATACGCCACGGGGGACGGGCCGAGTCGGACCCCTTCGAGTCCACACCTGTGTCGACGAGGCCCGGAACCTCC
 928 A  W  F  N  V  S  S  L  P  Y  A  V  P  P  L  S  L  P  R  G  E  A  Q  V  W  T  Q  L  L  R  A  L  E  E hphI      mseI
         mnlI      aluI
                   hindIII
3001 AGAGGTGATGAAAGCTT
     TCTCCACTACTTTCGAA
 962 R  O
```

```
                                                                    sau96I
                                                                    avaII
                                          aluI                scrFI
                                    sacI fokI              scrFI nlaIV          nlaIII
                                                  hgiAI  bstNI                  styI
                                                  bsp1286                       ncoI hinfI
                                                  banII
1001 TCAATTGATCTTGCAGTGACTGAAAATGTAGTCAATCTCATCAGAACTATAGTGAGCTCATCCCAGGACCACAGTGGGGTTCTGTCCATGATTC
     AGTTAACTAGAACGTCACTGACTTTTACATCAGTTAGAGATAGTCTTGATATCACTCGAGTAGGGTCCTGGTGTCACCCCAAGACAGGTACTTAAG
305    N   L   I   F   A   V   T   E   N   V   V   N   L   Y   Q   N   Y   S   E   L   I   P   G   T   T   V   G   V   L   S   M   D   S mnlI aluI             sfaNI                     aluI               mnlI                             mboII
1101 CAGCAATGCTCCTGCAGCTCATTGTGATGCTTATGGGAAAATCCGTTCTAAGTAGAGCTGGAAGTGCGTGACCTCCCTGAAGAGTTGTCTCTATCCTTC
     GTCGTTACGAGGACGTCGAGTAACATACGAATACCCTTTTAGGCAAGATTCATCTCGACCTTCACGCACTGGAGGACTTCTCAACAGAGATAGGAAG
338    S   N   V   L   Q   L   I   V   D   A   Y   G   K   I   R   S   K   V   E   L   E   V   R   D   L   P   E   E   L   S   L   S   F styI
                                                  haeIII                                                  haeIII
                                                  scrFI                                             pleI            haeI
                             mnlI                 bstNI                                             hinfI           mnlI
1201 AATGCCACTGCTCAACAATGAGGTCATCCTGGCCTCAAGTCTTGTATGGGACTCAAGATTGGAGACGCCGTGAGCTTCAGCATTGAGGCCAAGTGC
     TTACGGTGACGAGTTGTTACTCCAGTAGGACCGGAGTTCAGAACATACCCTGAGTTCTAACCCTCTGCCACTCGAAGTCGTAACTCCGGTTCACG
371   N   A   T   C   L   N   N   E   V   I   P   G   L   K   S   C   M   G   L   K   I   G   D   T   V   S   F   S   I   E   A   K   V   R hphI
                 scrFI                                                sau3AI  scrFI
                 bstNI                                                mboI    bstEII
                 mnlI                                                 dpnI  bstNI                                         bglI
1301 GAGGCTGTCCCCAGGAGAAGAAGTCCTTTACCATAAAGCCCGTGGGCTTCAAGGACAGCCTTCAGTGATCCTCCAGTCCACCTTTGATTGTGACTGTGCCTG
     CTCCGACAGGGGTCCTCTTCTTCAGGAAATGGTATTTCGGGCACCCGAAGTTCCTGTCGGACAGTCAGGTGGAAACTAACACTGACACGGAC
405    G   C   P   Q   E   K   K   S   F   T   I   K   P   V   G   F   K   D   S   L   I   V   Q   V   T   F   D   C   D   C   A   C sau3AI
                                                                       mboI
                                                                       dpnI
                                                      sau96I           alwI
                                                      avaII            xhoI
                                           ppuMI                       nlaIV
                                           nlaIV                       bstNI
                 sau96I                    eco0109I                    bglI            bamHI
                 haeIII                             fnu4HI                   scrFI     haeIII     alwI
        scrFI                                       bbvI                               sau96I
        bstNI     aluI
1401 CCAGGCCCAAGCTGAACTAATGCCTGCAACATGGCAATGCTGTCCTGAGGCCTTTGAGTGTGGGGGTATGCCGTTGTGGGCCTGGCTGGCTGGATCCCAG
     GGTCCGGGTTCGACTTGATTACGGACGTTGTTACCCTTACGACAGGACTCCGGAAACTCACACCCCATACGGCAACACCCGGACCGACCCTAGGGTC
438    Q   A   Q   A   E   P   N   S   H   R   C   N   N   G   N   G   T   F   E   C   G   V   R   C   G   P   G   W   L   G   S   Q
```

Fig.2(d)

```
                    ddeI                                                    fnu4HI
                    hgiAI                                   fnu4HI          bbvI
                    bsp1286                   mnlI          bbvI    avaI mnlI    pstI bglI           mnlI
1501 TGTGAGTGCTCAGAGGACGAGGACTATCGCCCTTCCCAGCAGGACGAGTGCAGCCCCGAGAGGTCAGCCAGCCCGTGCAGCCAGGGGGGGAGTGCCTCTGTG
     ACACTCACGAGTCTCCTGCTCCTGATAGCGGGAAGGGTCGTCCTGCTCACGTCGGGGCTCCCAGTGCGGTCGGTCGGGCACGTCGGTCCCCCTCACGAGACAC
                                                                                                    ddeI
                                                                                                    hgiAI
                                                                                                    bsp1286
471  C E C S E E D Y R P S Q Q D E C S P R E G Q P V C S Q R G E C L C G sau3AI                                                rsaI
                                mboI                                                  thaI
                                dpnI              rsaI
                                                  scaI
1601 GTCAATGTGTCGCCACAGCAGTGACTTTGGCAAGATCACGGGCAAGTACTGCGAGTGTGACGACTTCTCCTGTCGTCCGTACAAGGGGAGATGTGCTC
     CAGTTACACAGCGGTGTCGTCACTGAAACCGTTCTAGTGCCCGTTCATGACGCTCACACTGCTGAAGAGGACACAGGCAGGCAGGATGTTCCCCCTCTACACGAG
505  Q C V C H S S D F G K I T G K Y C E C D D F S C V R Y K G E M C S mspI                rsaI
         haeIII                                           sau96I              thaI
         haeI                                             avaII
         eaeI                         pleI                                    bstUI
     nlaIII                 aluI      hinfI     hpaII               rsaI mluI          bspMI
     styI               pvuII
     ncoI               fnu4HI
     haeIII    haeI     bbvI
1701 AGGCCATGGCCAGTGCAGCTGTGGGACTGCCTGTGACTCCGACTGGCTACTACTGCAACTGTACCACCGCTACTGACACTGTGACACCTGACTGTGCATCCAGC
     TCCGGTACCGGTCACGTCGACACCCCTGACGGACACTGAGGCTGACCGATGATGACGTTGACATGGTGCGCGATGACTGTGACGTACAGGTCG
                                thaI
                                sacII                                       nlaIV
                                fnu4HI
                                xmaIII                                      bsp1286
                                                                            banII
                    eaeI  fnu4HI                                            scrFI
                    notI bstUI                                              ncII
                    fnu4HI                        aluI                      mspI
                    bbvI         fnu4HI           pvuII                     hpaII
538  G H G Q C S C G D C L C D S D W T G Y Y C N C T T R T D T C M S S
                                                  fnu4HI
                                                  bbvI
1801 AATGGGCGCTGTGCAGGCTGCGGCAAGTGCGAATGTGGAATGTGGAAGCAGCAGTGTCTGTATCCAGCGGGGCTCCTATGGGACACCTGTGAGAAGTGCCCCACCT
     TTACCCGACGACACGTCCGACGCCGTTCACACTTACACCTTCATCACAGACATAGGTCGCCCGAGGATACCCTGTGGACACTCTTCACGGGGTGGA
                                                                            bsp1286
                                                                            banII
                                                                            nlaIV
                                                                            scrFI
                                                                            ncII
                                                                            mspI          bspMI
                                                                            hpaII         nlaIII
571  N G L L C S G R G K C E C G S C V C I Q P G S Y G D T C E K C P T C
                                                    nlaIII                bspMI
     sfaNI     mseI
1901 GCCCAGATGCCTCACCTTTAAGAAAGAATGTGGAGTGTAAGAAGTTTGACCGGACGCCCTACATGACCGAAAATACCTGCAACCGTTACTGCCGTGA
     CGGGTCTACGGAGTGGAAATTCTTTCTTACACCTCACATTCTTCAAACTGGCCTGCGGGATGTACTGGCTTTATGACGTTGGCAATGACGGCACT
605  P D A C T F K K E C V E C K K F D R E P Y M T E N T C N R Y C R D
```

Fig.2(e)

```
                   mseI                           sfaNI                            tthlllI
        pleI       aluI                foki                          foki          hinfI  scaI       rsaI
        hinfI      aflII       bsrI    rsaI                          mnlI          hinfI  scaI
2001 CGAGATTGAGTGACTCAGTCACTGTCAAAGAGCTTAAGGACACTGGCAAGGATGAAGTCAGTGAATGTACCTATAAGAATGAGGATGACTGTCGTGACACAGCAGATTCCAGTACTAT
     GCTCTAACTCACTGAGTCAGTGACAGTTTCTCGAATTCCTGTGACCGTTCCTACTTCAGTCACTTACATGGATATTCTTACTCCTACTGACACAGCAGTCTAAGGTCATGATA
 638  E  I  E  S  V  K  E  L  K  D  T  G  K  D  A  V  N  C  T  Y  K  N  E  D  D  C  V  V  R  F  Q  Y  Y sau96I
                                                   haeIII
                                                   sau96I
                                                   nlaIV eco0109I                  ddeI
                                                              bsp1286                   sau3AI
                                                              banII                     mboI
                                                        apaI                            dpnI           aluI
                                                        ecoO109I                        xhoII          bglII hindIII    mseI
              hinfI                                              styI             mboII                                bglII hindIII
        mboII          foki                                    mboII
2101 GAAGATTCTAGTGGAAAGTCCATCCTGTATGTGGTAGAAGAGCCAGAGTGTCCCAAGGGCCCTGACTGATGAGATCTAAGCTT
     CTTCTAAGATCACCTTTCAGTAGGACATACACCATCTTCTCGGTCTCACAGGGTTCCCGGGACTGACTACTCTAGATTCGAA
 671  E  D  S  S  G  K  S  I  L  Y  V  V  E  E  P  E  C  P  K  G  P  D  D  Q
```

Fig. 3.

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 3017 base pairs
        ( B ) TYPE: Nucleic Acid
        ( C ) STRANDEDNESS: Double
        ( D ) TOPOLOGY: Linear ( x i ) SEQUENCE DESCRIPTION: SEQ ID NO:1:

```
GAATTCTCGA GCTCGTCGAC CGGAAG      ATG GCC AGA GCT TTG   41
                                  Met Ala Arg Ala Leu
                                  -31 -30

TGT CCA CTG CAA GCC CTC TGG CTT CTG GAG TGG GTG CTG    80
Cys Pro Leu Gln Ala Leu Trp Leu Leu Glu Trp Val Leu
    -25                 -20                     -15

CTG CTC TTG GGA CCT TGT GCT GCC CCT CCA GCC TGG GCC   119
Leu Leu Leu Gly Pro Cys Ala Ala Pro Pro Ala Trp Ala
            -10                 -5

TTG AAC CTG GAC CCA GTG CAG CTC ACC TTC TAT GCA GGC   158
Leu Asn Leu Asp Pro Val Gln Leu Thr Phe Tyr Ala Gly
 1           5                   10

CCC AAT GGC AGC CAG TTT GGA TTT TCA CTG GAC TTC CAC   197
Pro Asn Gly Ser Gln Phe Gly Phe Ser Leu Asp Phe His
        15              20                      25

AAG GAC AGC CAT GGG AGA GTG GCC ATC GTG GTG GGC GCC   236
Lys Asp Ser His Gly Arg Val Ala Ile Val Val Gly Ala
            30                  35

CCG CGG ACC CTG GGC CCC AGC CAG GAG GAG ACG GGC GGC   275
Pro Arg Thr Leu Gly Pro Ser Gln Glu Glu Thr Gly Gly
```

```
             40                        45                          50
    GTG TTC CTG TGC CCC TGG AGG GCC GAG GGC GGC CAG TGC   314
    Val Phe Leu Cys Pro Trp Arg Ala Glu Gly Gly Gln Cys
            55                      60                      65

CCC TCG CTG CTC TTT GAC CTC CGT GAT GAG ACC CGA AAT   353
    Pro Ser Leu Leu Phe Asp Leu Arg Asp Glu Thr Arg Asn
                    70                      75

GTA GGC TCC CAA ACT TTA CAA ACC TTC AAG GCC CGC CAA   392
    Val Gly Ser Gln Thr Leu Gln Thr Phe Lys Ala Arg Gln
            80                      85                      90

GGA CTG GGG GCG TCG GTC GTC AGC TGG AGC GAC GTC ATT   431
    Gly Leu Gly Ala Ser Val Val Ser Trp Ser Asp Val Ile
                    95                      100

GTG GCC TGC GCC CCC TGG CAG CAC TGG AAC GTC CTA GAA   470
    Val Ala Cys Ala Pro Trp Gln His Trp Asn Val Leu Glu
    105                     110                     115

AAG ACT GAG GAG GCT GAG AAG ACG CCC GTA GGT AGC TGC   509
    Lys Thr Glu Glu Ala Glu Lys Thr Pro Val Gly Ser Cys
                    120                     125                     130

TTT TTG GCT CAG CCA GAG AGC GGC CGC CGC GCC GAG TAC   548
    Phe Leu Ala Gln Pro Glu Ser Gly Arg Arg Ala Glu Tyr
                    135                     140

TCC CCC TGT CGC GGG AAC ACC CTG AGC CGC ATT TAC GTG   587
    Ser Pro Cys Arg Gly Asn Thr Leu Ser Arg Ile Tyr Val
    145                     150                     155

GAA AAT GAT TTT AGC TGG GAC AAG CGT TAC TGT GAA GCG   626
    Glu Asn Asp Phe Ser Trp Asp Lys Arg Tyr Cys Glu Ala
                    160                     165

GGC TTC AGC TCC GTG GTC ACT CAG GCC GGA GAG CTG GTG   665
    Gly Phe Ser Ser Val Val Thr Gln Ala Gly Glu Leu Val
    170                     175                     180

CTT GGG GCT CCT GGC GGC TAT TAT TTC TTA GGT CTC CTG   704
    Leu Gly Ala Pro Gly Gly Tyr Tyr Phe Leu Gly Leu Leu
                    185                     190                     195

GCC CAG GCT CCA GTT GCG GAT ATT TTC TCG AGT TAC CGC   743
    Ala Gln Ala Pro Val Ala Asp Ile Phe Ser Ser Tyr Arg
                    200                     205

CCA GGC ATC CTT TTG TGG CAC GTG TCC TCC CAG AGC CTC   782
    Pro Gly Ile Leu Leu Trp His Val Ser Ser Gln Ser Leu
    210                     215                     220

TCC TTT GAC TCC AGC AAC CCA GAG TAC TTC GAC GGC TAC   821
    Ser Phe Asp Ser Ser Asn Pro Glu Tyr Phe Asp Gly Tyr
                    225                     230

TGG GGG TAC TCG GTG GCC GTG GGC GAG TTC GAC GGG GAT   860
    Trp Gly Tyr Ser Val Ala Val Gly Glu Phe Asp Gly Asp
    235                     240                     245

CTC AAC ACT ACA GAA TAT GTC GTC GGT GCC CCC ACT TGG   899
    Leu Asn Thr Thr Glu Tyr Val Val Gly Ala Pro Thr Trp
                    250                     255                     260

AGC TGG ACC CTG GGA GCG GTG GAA ATT TTG GAT TCC TAC   938
    Ser Trp Thr Leu Gly Ala Val Glu Ile Leu Asp Ser Tyr
                    265                     270

TAC CAG AGG CTG CAT CGG CTG CGC GCA GAG CAG ATG GCG   977
    Tyr Gln Arg Leu His Arg Leu Arg Ala Glu Gln Met Ala
    275                     280                     285

TCG TAT TTT GGG CAT TCA GTG GCT GTC ACT GAC GTC AAC   1016
    Ser Tyr Phe Gly His Ser Val Ala Val Thr Asp Val Asn
                    290                     295

GGG GAT GGG AGG CAT GAT CTG CTG GTG GGC GCT CCA CTG   1055
    Gly Asp Gly Arg His Asp Leu Leu Val Gly Ala Pro Leu
```

```
                300                      305                         310
TAT ATG GAG AGC CGG GCA GAC CGA AAA CTG GCC GAA GTG  1094
Tyr Met Glu Ser Arg Ala Asp Arg Lys Leu Ala Glu Val
            315                 320                    325

GGG CGT GTG TAT TTG TTC CTG CAG CCG CGA GGC CCC CAC  1133
Gly Arg Val Tyr Leu Phe Leu Gln Pro Arg Gly Pro His
                330                  335

GCG CTG GGT GCC CCC AGC CTC CTG CTG ACT GGC ACA CAG  1172
Ala Leu Gly Ala Pro Ser Leu Leu Leu Thr Gly Thr Gln
        340                  345                350

CTC TAT GGG CGA TTC GGC TCT GCC ATC GCA CCC CTG GGC  1211
Leu Tyr Gly Arg Phe Gly Ser Ala Ile Ala Pro Leu Gly
                355                  360

GAC CTC GAC CGG GAT GGC TAC AAT GAC ATT GCA GTG GCT  1250
Asp Leu Asp Arg Asp Gly Tyr Asn Asp Ile Ala Val Ala
365                 370                  375

GCC CCC TAC GGG GGT CCC AGT GGC CGG GGC CAA GTG CTG  1289
Ala Pro Tyr Gly Gly Pro Ser Gly Arg Gly Gln Val Leu
            380                  385                  390

GTG TTC CTG GGT CAG AGT GAG GGG CTG AGG TCA CGT CCC  1328
Val Phe Leu Gly Gln Ser Glu Gly Leu Arg Ser Arg Pro
                395                  400

TCC CAG GTC CTG GAC AGC CCC TTC CCC ACA GGC TCT GCC  1367
Ser Gln Val Leu Asp Ser Pro Phe Pro Thr Gly Ser Ala
        405                  410                 415

TTT GGC TTC TCC CTT CGA GGT GCC GTA GAC ATC GAT GAC  1406
Phe Gly Phe Ser Leu Arg Gly Ala Val Asp Ile Asp Asp
                420                  425

AAC GGA TAC CCA GAC CTG ATC GTG GGA GCT TAC GGG GCC  1445
Asn Gly Tyr Pro Asp Leu Ile Val Gly Ala Tyr Gly Ala
430                 435                  440

AAC CAG GTG GCT GTG TAC AGA GCT CAG CCA GTG GTG AAG  1484
Asn Gln Val Ala Val Tyr Arg Ala Gln Pro Val Val Lys
            445                  450                  455

GCC TCT GTC CAG CTA CTG GTG CAA GAT TCA CTG AAT CCT  1523
Ala Ser Val Gln Leu Leu Val Gln Asp Ser Leu Asn Pro
                460                  465

GCT GTG AAG AGC TGT GTC CTA CCT CAG ACC AAG ACA CCC  1562
Ala Val Lys Ser Cys Val Leu Pro Gln Thr Lys Thr Pro
        470                  475                 480

GTG AGC TGC TTC AAC ATC CAG ATG TGT GTT GGA GCC ACT  1601
Val Ser Cys Phe Asn Ile Gln Met Cys Val Gly Ala Thr
                485                  490

GGG CAC AAC ATT CCT CAG AAG CTA TCC CTA AAT GCC GAG  1640
Gly His Asn Ile Pro Gln Lys Leu Ser Leu Asn Ala Glu
495                 500                  505

CTG CAG CTG GAC CGG CAG AAG CCC CGC CAG GGC CGG CGG  1679
Leu Gln Leu Asp Arg Gln Lys Pro Arg Gln Gly Arg Arg
            510                  515                  520

GTG CTG CTG CTG GGC TCT CAA CAG GCA GGC ACC ACC CTG  1718
Val Leu Leu Leu Gly Ser Gln Gln Ala Gly Thr Thr Leu
                525                  530

AAC CTG GAT CTG GGC GGA AAG CAC AGC CCC ATC TGC CAC  1757
Asn Leu Asp Leu Gly Gly Lys His Ser Pro Ile Cys His
        535                  540                 545

ACC ACC ATG GCC TTC CTT CGA GAT GAG GCA GAC TTC CGG  1796
Thr Thr Met Ala Phe Leu Arg Asp Glu Ala Asp Phe Arg
                550                  555

GAC AAG CTG AGC CCC ATT GTG CTC AGC CTC AAT GTG TCC  1835
Asp Lys Leu Ser Pro Ile Val Leu Ser Leu Asn Val Ser
```

-continued

```
       560                          565                           570
CTA  CCG  CCC  ACG  GAG  GCT  GGA  ATG  GCC  CCT  GCT  GTC  GTG   1874
Leu  Pro  Pro  Thr  Glu  Ala  Gly  Met  Ala  Pro  Ala  Val  Val
          575                      580                       585

CTG  CAT  GGA  GAC  ACC  CAT  GTG  CAG  GAG  CAG  ACA  CGA  ATC   1913
Leu  His  Gly  Asp  Thr  His  Val  Gln  Glu  Gln  Thr  Arg  Ile
                    590                      595

GTC  CTG  GAC  TGT  GGG  GAA  GAT  GAC  GTA  TGT  GTG  CCC  CAG   1952
Val  Leu  Asp  Cys  Gly  Glu  Asp  Asp  Val  Cys  Val  Pro  Gln
          600                      605                      610

CTT  CAG  CTC  ACT  GCC  AGC  GTG  ACG  GGC  TCC  CCG  CTC  CTA   1991
Leu  Gln  Leu  Thr  Ala  Ser  Val  Thr  Gly  Ser  Pro  Leu  Leu
                    615                      620

GTT  GGG  GCA  GAT  AAT  GTC  CTG  GAG  CTG  CAG  ATG  GAC  GCA   2030
Val  Gly  Ala  Asp  Asn  Val  Leu  Glu  Leu  Gln  Met  Asp  Ala
625                      630                      635

GCC  AAC  GAG  GGC  GAG  GGG  GCC  TAT  GAA  GCA  GAG  CTG  GCC   2069
Ala  Asn  Glu  Gly  Glu  Gly  Ala  Tyr  Glu  Ala  Glu  Leu  Ala
                    640                      645                 650

GTG  CAC  CTG  CCC  CAG  GGC  GCC  CAC  TAC  ATG  CGG  GCC  CTA   2108
Val  His  Leu  Pro  Gln  Gly  Ala  His  Tyr  Met  Arg  Ala  Leu
                         655                      660

AGC  AAT  GTC  GAG  GGC  TTT  GAG  AGA  CTC  ATC  TGT  AAT  CAG   2147
Ser  Asn  Val  Glu  Gly  Phe  Glu  Arg  Leu  Ile  Cys  Asn  Gln
     665                      670                      675

AAG  AAG  GAG  AAT  GAG  ACC  AGG  GTG  GTG  CTG  TGT  GAG  CTG   2186
Lys  Lys  Glu  Asn  Glu  Thr  Arg  Val  Val  Leu  Cys  Glu  Leu
               680                      685

GGC  AAC  CCC  ATG  AAG  AAG  AAC  GCC  CAG  ATA  GGA  ATC  GCG   2225
Gly  Asn  Pro  Met  Lys  Lys  Asn  Ala  Gln  Ile  Gly  Ile  Ala
690                      695                      700

ATG  TTG  GTG  AGC  GTG  GGG  AAT  CTG  GAA  GAG  GCT  GGG  GAG   2264
Met  Leu  Val  Ser  Val  Gly  Asn  Leu  Glu  Glu  Ala  Gly  Glu
          705                      710                      715

TCT  GTG  TCC  TTC  CAG  CTG  CAG  ATA  CGG  AGC  AAG  AAC  AGC   2303
Ser  Val  Ser  Phe  Gln  Leu  Gln  Ile  Arg  Ser  Lys  Asn  Ser
                    720                      725

CAG  AAT  CCA  AAC  AGC  AAG  ATT  GTG  CTG  CTG  GAC  GTG  CCG   2342
Gln  Asn  Pro  Asn  Ser  Lys  Ile  Val  Leu  Leu  Asp  Val  Pro
          730                      735                      740

GTC  CGG  GCA  GAG  GCC  CAA  GTG  GAG  CTG  CGA  GGG  AAC  TCC   2381
Val  Arg  Ala  Glu  Ala  Gln  Val  Glu  Leu  Arg  Gly  Asn  Ser
               745                      750

TTT  CCA  GCC  TCC  CTG  GTG  GTG  GCA  GCA  GAA  GAA  GGT  GAG   2420
Phe  Pro  Ala  Ser  Leu  Val  Val  Ala  Ala  Glu  Glu  Gly  Glu
755                      760                      765

AGG  GAG  CAG  AAC  AGC  TTG  GAC  AGC  TGG  GGA  CCC  AAA  GTG   2459
Arg  Glu  Gln  Asn  Ser  Leu  Asp  Ser  Trp  Gly  Pro  Lys  Val
          770                      775                      780

GAG  CAC  ACC  TAT  GAG  CTC  CAC  AAC  AAT  GGC  CCT  GGG  ACT   2498
Glu  His  Thr  Tyr  Glu  Leu  His  Asn  Asn  Gly  Pro  Gly  Thr
                    785                      790

GTG  AAT  GGT  CTT  CAC  CTC  AGC  ATC  CAC  CTT  CCG  GGA  CAG   2537
Val  Asn  Gly  Leu  His  Leu  Ser  Ile  His  Leu  Pro  Gly  Gln
795                      800                      805

TCC  CAG  CCC  TCC  GAC  CTG  CTC  TAC  ATC  CTG  GAT  ATA  CAG   2576
Ser  Gln  Pro  Ser  Asp  Leu  Leu  Tyr  Ile  Leu  Asp  Ile  Gln
                    810                      815

CCC  CAG  GGG  GGC  CTT  CAG  TGC  TTC  CCA  CAG  CCT  CCT  GTC   2615
Pro  Gln  Gly  Gly  Leu  Gln  Cys  Phe  Pro  Gln  Pro  Pro  Val
```

```
                      825                           830
820
AAC  CCT  CTC  AAG  GTG  GAC  TGG  GGG  CTG  CCC  ATC  CCC  AGC  2654
Asn  Pro  Leu  Lys  Val  Asp  Trp  Gly  Leu  Pro  Ile  Pro  Ser
               835                      840                 845

CCC  TCC  CCC  ATT  CAC  CCG  GCC  CAT  CAC  AAG  CGG  GAT  CGC  2693
Pro  Ser  Pro  Ile  His  Pro  Ala  His  His  Lys  Arg  Asp  Arg
                    850                      855

AGA  CAG  ATC  TTC  CTG  CCA  GAG  CCC  GAG  CAG  CCC  TCG  AGG  2732
Arg  Gln  Ile  Phe  Leu  Pro  Glu  Pro  Glu  Gln  Pro  Ser  Arg
          860                     865                     870

CTT  CAG  GAT  CCA  GTT  CTC  GTA  AGC  TGC  GAC  TCG  GCG  CCC  2771
Leu  Gln  Asp  Pro  Val  Leu  Val  Ser  Cys  Asp  Ser  Ala  Pro
               875                      880

TGT  ACT  GTG  GTG  CAG  TGT  GAC  CTG  CAG  GAG  ATG  GCG  CGC  2810
Cys  Thr  Val  Val  Gln  Cys  Asp  Leu  Gln  Glu  Met  Ala  Arg
885                     890                     895

GGG  CAG  CGG  GCC  ATG  GTC  ACG  GTG  CTG  GCC  TTC  CTG  TGG  2849
Gly  Gln  Arg  Ala  Met  Val  Thr  Val  Leu  Ala  Phe  Leu  Trp
          900                     905                     910

CTG  CCC  AGC  CTC  TAC  CAG  AGG  CCT  CTG  GAT  CAG  TTT  GTG  2888
Leu  Pro  Ser  Leu  Tyr  Gln  Arg  Pro  Leu  Asp  Gln  Phe  Val
                    915                      920

CTG  CAG  TCG  CAC  GCA  TGG  TTC  AAC  GTG  TCC  TCC  CTC  CCC  2927
Leu  Gln  Ser  His  Ala  Trp  Phe  Asn  Val  Ser  Ser  Leu  Pro
          925                     930                     935

TAT  GCG  GTG  CCC  CCG  CTC  AGC  CTG  CCC  CGA  GGG  GAA  GCT  2966
Tyr  Ala  Val  Pro  Pro  Leu  Ser  Leu  Pro  Arg  Gly  Glu  Ala
               940                      945

CAG  GTG  TGG  ACA  CAG  CTC  CTC  CGG  GCC  TTG  GAG  GAG  AGG  3005
Gln  Val  Trp  Thr  Gln  Leu  Leu  Arg  Ala  Leu  Glu  Glu  Arg
950                     955                     960       962

T GATG AAAGCTT 3017
```

( 2 ) INFORMATION FOR SEQ ID NO:2:

( i ) SEQUENCE CHARACTERISTICS:
        ( A ) LENGTH: 993 amino acids
        ( B ) TYPE: Amino Acid
        ( D ) TOPOLOGY: Linear ( x i ) SEQUENCE DESCRIPTION: SEQ ID NO:2:

```
Met  Ala  Arg  Ala  Leu  Cys  Pro  Leu  Gln  Ala  Leu  Trp  Leu  Leu  Glu
-31  -30                 -25                     -20

Trp  Val  Leu  Leu  Leu  Leu  Gly  Pro  Cys  Ala  Ala  Pro  Pro  Ala  Trp
     -15                     -10                      -5

Ala  Leu  Asn  Leu  Asp  Pro  Val  Gln  Leu  Thr  Phe  Tyr  Ala  Gly  Pro
     1                   5                    10

Asn  Gly  Ser  Gln  Phe  Gly  Phe  Ser  Leu  Asp  Phe  His  Lys  Asp  Ser
15                       20                   25

His  Gly  Arg  Val  Ala  Ile  Val  Val  Gly  Ala  Pro  Arg  Thr  Leu  Gly
30                       35                   40

Pro  Ser  Gln  Glu  Glu  Thr  Gly  Gly  Val  Phe  Leu  Cys  Pro  Trp  Arg
45                       50                   55

Ala  Glu  Gly  Gly  Gln  Cys  Pro  Ser  Leu  Leu  Phe  Asp  Leu  Arg  Asp
60                       65                   70

Glu  Thr  Arg  Asn  Val  Gly  Ser  Gln  Thr  Leu  Gln  Thr  Phe  Lys  Ala
75                       80                   85

Arg  Gln  Gly  Leu  Gly  Ala  Ser  Val  Val  Ser  Trp  Ser  Asp  Val  Ile
90                       95                   100
```

```
Val  Ala  Cys  Ala  Pro  Trp  Gln  His  Trp  Asn  Val  Leu  Glu  Lys  Thr
105                      110                      115
Glu  Glu  Ala  Glu  Lys  Thr  Pro  Val  Gly  Ser  Cys  Phe  Leu  Ala  Gln
120                      125                      130
Pro  Glu  Ser  Gly  Arg  Arg  Ala  Glu  Tyr  Ser  Pro  Cys  Arg  Gly  Asn
135                      140                      145
Thr  Leu  Ser  Arg  Ile  Tyr  Val  Glu  Asn  Asp  Phe  Ser  Trp  Asp  Lys
150                      155                      160
Arg  Tyr  Cys  Glu  Ala  Gly  Phe  Ser  Ser  Val  Val  Thr  Gln  Ala  Gly
165                      170                      175
Glu  Leu  Val  Leu  Gly  Ala  Pro  Gly  Gly  Tyr  Tyr  Phe  Leu  Gly  Leu
180                      185                      190
Leu  Ala  Gln  Ala  Pro  Val  Ala  Asp  Ile  Phe  Ser  Ser  Tyr  Arg  Pro
195                      200                      205
Gly  Ile  Leu  Leu  Trp  His  Val  Ser  Ser  Gln  Ser  Leu  Ser  Phe  Asp
210                      215                      220
Ser  Ser  Asn  Pro  Glu  Tyr  Phe  Asp  Gly  Tyr  Trp  Gly  Tyr  Ser  Val
225                      230                      235
Ala  Val  Gly  Glu  Phe  Asp  Gly  Asp  Leu  Asn  Thr  Thr  Glu  Tyr  Val
240                      245                      250
Val  Gly  Ala  Pro  Thr  Trp  Ser  Trp  Thr  Leu  Gly  Ala  Val  Glu  Ile
255                      260                      265
Leu  Asp  Ser  Tyr  Tyr  Gln  Arg  Leu  His  Arg  Leu  Arg  Ala  Glu  Gln
270                      275                      280
Met  Ala  Ser  Tyr  Phe  Gly  His  Ser  Val  Ala  Val  Thr  Asp  Val  Asn
285                      290                      295
Gly  Asp  Gly  Arg  His  Asp  Leu  Leu  Val  Gly  Ala  Pro  Leu  Tyr  Met
300                      305                      310
Glu  Ser  Arg  Ala  Asp  Arg  Lys  Leu  Ala  Glu  Val  Gly  Arg  Val  Tyr
315                      320                      325
Leu  Phe  Leu  Gln  Pro  Arg  Gly  Pro  His  Ala  Leu  Gly  Ala  Pro  Ser
330                      335                      340
Leu  Leu  Leu  Thr  Gly  Thr  Gln  Leu  Tyr  Gly  Arg  Phe  Gly  Ser  Ala
345                      350                      355
Ile  Ala  Pro  Leu  Gly  Asp  Leu  Asp  Arg  Asp  Gly  Tyr  Asn  Asp  Ile
360                      365                      370
Ala  Val  Ala  Ala  Pro  Tyr  Gly  Gly  Pro  Ser  Gly  Arg  Gly  Gln  Val
375                      380                      385
Leu  Val  Phe  Leu  Gly  Gln  Ser  Glu  Gly  Leu  Arg  Ser  Arg  Pro  Ser
390                      395                      400
Gln  Val  Leu  Asp  Ser  Pro  Phe  Pro  Thr  Gly  Ser  Ala  Phe  Gly  Phe
405                      410                      415
Ser  Leu  Arg  Gly  Ala  Val  Asp  Ile  Asp  Asp  Asn  Gly  Tyr  Pro  Asp
420                      425                      430
Leu  Ile  Val  Gly  Ala  Tyr  Gly  Ala  Asn  Gln  Val  Ala  Val  Tyr  Arg
435                      440                      445
Ala  Gln  Pro  Val  Val  Lys  Ala  Ser  Val  Gln  Leu  Leu  Val  Gln  Asp
450                      455                      460
Ser  Leu  Asn  Pro  Ala  Val  Lys  Ser  Cys  Val  Leu  Pro  Gln  Thr  Lys
465                      470                      475
Thr  Pro  Val  Ser  Cys  Phe  Asn  Ile  Gln  Met  Cys  Val  Gly  Ala  Thr
480                      485                      490
Gly  His  Asn  Ile  Pro  Gln  Lys  Leu  Ser  Leu  Asn  Ala  Glu  Leu  Gln
```

-continued

```
495                      500                       505
Leu Asp Arg Gln Lys  Pro Arg Gln Gly Arg  Arg Val Leu Leu Leu
510                  515                  520
Gly Ser Gln Gln Ala  Gly Thr Thr Leu Asn  Leu Asp Leu Gly Gly
525                  530                  535
Lys His Ser Pro Ile  Cys His Thr Thr Met  Ala Phe Leu Arg Asp
540                  545                  550
Glu Ala Asp Phe Arg  Asp Lys Leu Ser Pro  Ile Val Leu Ser Leu
555                  560                  565
Asn Val Ser Leu Pro  Pro Thr Glu Ala Gly  Met Ala Pro Ala Val
570                  575                  580
Val Leu His Gly Asp  Thr His Val Gln Glu  Gln Thr Arg Ile Val
585                  590                  595
Leu Asp Cys Gly Glu  Asp Val Cys Val Pro  Gln Leu Gln Leu
600                  605                  610
Thr Ala Ser Val Thr  Gly Ser Pro Leu Leu  Val Gly Ala Asp Asn
615                  620                  625
Val Leu Glu Leu Gln  Met Asp Ala Ala Asn  Glu Gly Glu Gly Ala
630                  635                  640
Tyr Glu Ala Glu Leu  Ala Val His Leu Pro  Gln Gly Ala His Tyr
645                  650                  655
Met Arg Ala Leu Ser  Asn Val Glu Gly Phe  Glu Arg Leu Ile Cys
660                  665                  670
Asn Gln Lys Lys Glu  Asn Glu Thr Arg Val  Val Leu Cys Glu Leu
675                  680                  685
Gly Asn Pro Met Lys  Lys Asn Ala Gln Ile  Gly Ile Ala Met Leu
690                  695                  700
Val Ser Val Gly Asn  Leu Glu Glu Ala Gly  Glu Ser Val Ser Phe
705                  710                  715
Gln Leu Gln Ile Arg  Ser Lys Asn Ser Gln  Asn Pro Asn Ser Lys
720                  725                  730
Ile Val Leu Leu Asp  Val Pro Val Arg Ala  Glu Ala Gln Val Glu
735                  740                  745
Leu Arg Gly Asn Ser  Phe Pro Ala Ser Leu  Val Val Ala Ala Glu
750                  755                  760
Glu Gly Glu Arg Glu  Gln Asn Ser Leu Asp  Ser Trp Gly Pro Lys
765                  770                  775
Val Glu His Thr Tyr  Glu Leu His Asn Asn  Gly Pro Gly Thr Val
780                  785                  790
Asn Gly Leu His Leu  Ser Ile His Leu Pro  Gly Gln Ser Gln Pro
795                  800                  805
Ser Asp Leu Leu Tyr  Ile Leu Asp Ile Gln  Pro Gln Gly Gly Leu
810                  815                  820
Gln Cys Phe Pro Gln  Pro Val Asn Pro Leu  Lys Val Asp Trp
825                  830                  835
Gly Leu Pro Ile Pro  Ser Pro Ser Pro Ile  His Pro Ala His His
840                  845                  850
Lys Arg Asp Arg Arg  Gln Ile Phe Leu Pro  Glu Pro Glu Gln Pro
855                  860                  865
Ser Arg Leu Gln Asp  Pro Val Leu Val Ser  Cys Asp Ser Ala Pro
870                  875                  880
Cys Thr Val Val Gln  Cys Asp Leu Gln Glu  Met Ala Arg Gly Gln
885                  890                  895
```

| | | | | | | | | | | | | | |
|---|---|---|---|---|---|---|---|---|---|---|---|---|---|
| Arg | Ala | Met | Val | Thr | Val | Leu | Ala | Phe | Leu | Trp | Leu | Pro | Ser | Leu |
| 900 | | | | | 905 | | | | | 910 | | | | |
| Tyr | Gln | Arg | Pro | Leu | Asp | Gln | Phe | Val | Leu | Gln | Ser | His | Ala | Trp |
| 915 | | | | | 920 | | | | | 925 | | | | |
| Phe | Asn | Val | Ser | Ser | Leu | Pro | Tyr | Ala | Val | Pro | Pro | Leu | Ser | Leu |
| 930 | | | | | 935 | | | | | 940 | | | | |
| Pro | Arg | Gly | Glu | Ala | Gln | Val | Trp | Thr | Gln | Leu | Leu | Arg | Ala | Leu |
| 945 | | | | | 950 | | | | | 955 | | | | |
| Glu | Glu | Arg | | | | | | | | | | | | |
| 960 | | 962 | | | | | | | | | | | | |

( 2 ) INFORMATION FOR SEQ ID NO:3:

( i ) SEQUENCE CHARACTERISTICS:
        ( A ) LENGTH: 2183 base pairs
        ( B ) TYPE: Nucleic Acid
        ( C ) STRANDEDNESS: Double
        ( D ) TOPOLOGY: Linear ( x i ) SEQUENCE DESCRIPTION: SEQ ID NO:3:

```
TCTAGAGCCG CC   ATG  AGA  GCA  CGT  CCT  CGA  CCA  CGT  CCT    39
                Met  Arg  Ala  Arg  Pro  Arg  Pro  Arg  Pro
                -26  -25                 -20

CTC  TGG  GCG  ACT  GTG  CTG  GCA  CTG  GGA  GCA  CTG  GCT  GGT    78
Leu  Trp  Ala  Thr  Val  Leu  Ala  Leu  Gly  Ala  Leu  Ala  Gly
          -15                 -10                           -5

GTT  GGA  GTA  GGA  GGG  CCC  AAC  ATC  TGT  ACC  ACG  CGA  GGT   117
Val  Gly  Val  Gly  Gly  Pro  Asn  Ile  Cys  Thr  Thr  Arg  Gly
                     1                    5

GTG  AGC  TCC  TGC  CAG  CAG  TGC  CTG  GCT  GTG  AGC  CCC  ATG   156
Val  Ser  Ser  Cys  Gln  Gln  Cys  Leu  Ala  Val  Ser  Pro  Met
10                    15                   20

TGT  GCC  TGG  TGC  TCT  GAT  GAG  GCC  CTG  CCT  CTG  GGC  TCA   195
Cys  Ala  Trp  Cys  Ser  Asp  Glu  Ala  Leu  Pro  Leu  Gly  Ser
               25                   30                        35

CCT  CGC  TGT  GAC  CTG  AAG  GAG  AAT  CTG  CTG  AAG  GAT  AAC   234
Pro  Arg  Cys  Asp  Leu  Lys  Glu  Asn  Leu  Leu  Lys  Asp  Asn
                    40                        45

TGT  GCC  CCA  GAA  TCC  ATC  GAG  TTC  CCA  GTG  AGT  GAG  GCC   273
Cys  Ala  Pro  Glu  Ser  Ile  Glu  Phe  Pro  Val  Ser  Glu  Ala
50                        55                        60

CGA  GTA  CTA  GAG  GAC  AGG  CCC  CTC  AGC  GAC  AAG  GGC  TCT   312
Arg  Val  Leu  Glu  Asp  Arg  Pro  Leu  Ser  Asp  Lys  Gly  Ser
                65                        70

GGA  GAC  AGC  TCC  CAG  GTC  ACT  CAA  GTC  AGT  CCC  CAG  AGG   351
Gly  Asp  Ser  Ser  Gln  Val  Thr  Gln  Val  Ser  Pro  Gln  Arg
75                   80                        85

ATT  GCA  CTC  CGG  CTC  CGG  CCA  GAT  GAT  TCG  AAG  AAT  TTC   390
Ile  Ala  Leu  Arg  Leu  Arg  Pro  Asp  Asp  Ser  Lys  Asn  Phe
               90                   95                       100

TCC  ATC  CAA  GTG  CGG  CAG  GTG  GAG  GAT  TAC  CCT  GTG  GAC   429
Ser  Ile  Gln  Val  Arg  Gln  Val  Glu  Asp  Tyr  Pro  Val  Asp
                    105                       110

ATC  TAC  TAC  TTG  ATG  GAC  CTG  TCT  TAC  TCC  ATG  AAG  GAT   468
Ile  Tyr  Tyr  Leu  Met  Asp  Leu  Ser  Tyr  Ser  Met  Lys  Asp
115                       120                       125

GAT  CTG  TGG  AGC  ATC  CAG  AAC  CTG  GGT  ACC  AAG  CTG  GCC   507
Asp  Leu  Trp  Ser  Ile  Gln  Asn  Leu  Gly  Thr  Lys  Leu  Ala
               130                       135

ACC  CAG  ATG  CGA  AAG  CTC  ACC  AGT  AAC  CTG  CGG  ATT  GGC   546
Thr  Gln  Met  Arg  Lys  Leu  Thr  Ser  Asn  Leu  Arg  Ile  Gly
```

-continued

```
        140                      145                         150
    TTC GGG GCA TTT GTG GAC AAG CCT GTG TCA CCA TAC ATG    585
    Phe Gly Ala Phe Val Asp Lys Pro Val Ser Pro Tyr Met
            155             160                 165

TAT ATC TCC CCA CCA GAG GCC CTC GAA AAC CCC TGC TAT    624
    Tyr Ile Ser Pro Pro Glu Ala Leu Glu Asn Pro Cys Tyr
                    170             175

GAT ATG AAG ACC ACC TGC TTG CCC ATG TTT GGC TAC AAA    663
    Asp Met Lys Thr Thr Cys Leu Pro Met Phe Gly Tyr Lys
    180             185                 190

CAC GTG CTG ACG CTA ACT GAC CAG GTG ACC CGC TTC AAT    702
    His Val Leu Thr Leu Thr Asp Gln Val Thr Arg Phe Asn
                195             200

GAG GAA GTG AAG AAG CAG AGT GTG TCA CGG AAC CGA GAT    741
    Glu Glu Val Lys Lys Gln Ser Val Ser Arg Asn Arg Asp
    205             210                 215

GCC CCA GAG GGT GGC TTT GAT GCC ATC ATG CAG GCT ACA    780
    Ala Pro Glu Gly Gly Phe Asp Ala Ile Met Gln Ala Thr
                220             225             230

GTC TGT GAT GAA AAG ATT GGC TGG AGG AAT GAT GCA TCC    819
    Val Cys Asp Glu Lys Ile Gly Trp Arg Asn Asp Ala Ser
                    235             240

CAC TTG CTG GTG TTT ACC ACT GAT GCC AAG ACT CAT ATA    858
    His Leu Leu Val Phe Thr Thr Asp Ala Lys Thr His Ile
    245             250                 255

GCA TTG GAC GGA AGG CTG GCA GGC ATT GTC CAG CCT AAT    897
    Ala Leu Asp Gly Arg Leu Ala Gly Ile Val Gln Pro Asn
                260             265

GAC GGG CAG TGT CAT GTT GGT AGT GAC AAT CAT TAC TCT    936
    Asp Gly Gln Cys His Val Gly Ser Asp Asn His Tyr Ser
    270             275                 280

GCC TCC ACT ACC ATG GAT TAT CCC TCT TTG GGG CTG ATG    975
    Ala Ser Thr Thr Met Asp Tyr Pro Ser Leu Gly Leu Met
            285             290                 295

ACT GAG AAG CTA TCC CAG AAA AAC ATC AAT TTG ATC TTT   1014
    Thr Glu Lys Leu Ser Gln Lys Asn Ile Asn Leu Ile Phe
                    300             305

GCA GTG ACT GAA AAT GTA GTC AAT CTC TAT CAG AAC TAT   1053
    Ala Val Thr Glu Asn Val Val Asn Leu Tyr Gln Asn Tyr
    310             315                 320

AGT GAG CTC ATC CCA GGG ACC ACA GTT GGG GTT CTG TCC   1092
    Ser Glu Leu Ile Pro Gly Thr Thr Val Gly Val Leu Ser
                325             330

ATG GAT TCC AGC AAT GTC CTC CAG CTC ATT GTT GAT GCT   1131
    Met Asp Ser Ser Asn Val Leu Gln Leu Ile Val Asp Ala
    335             340                 345

TAT GGG AAA ATC CGT TCT AAA GTA GAG CTG GAA GTG CGT   1170
    Tyr Gly Lys Ile Arg Ser Lys Val Glu Leu Glu Val Arg
            350             355                 360

GAC CTC CCT GAA GAG TTG TCT CTA TCC TTC AAT GCC ACC   1209
    Asp Leu Pro Glu Glu Leu Ser Leu Ser Phe Asn Ala Thr
                    365             370

TGC CTC AAC AAT GAG GTC ATC CCT GGC CTC AAG TCT TGT   1248
    Cys Leu Asn Asn Glu Val Ile Pro Gly Leu Lys Ser Cys
    375             380                 385

ATG GGA CTC AAG ATT GGA GAC ACG GTG AGC TTC AGC ATT   1287
    Met Gly Leu Lys Ile Gly Asp Thr Val Ser Phe Ser Ile
                390             395

GAG GCC AAG GTG CGA GGC TGT CCC CAG GAG AAG GAG AAG   1326
    Glu Ala Lys Val Arg Gly Cys Pro Gln Glu Lys Glu Lys
```

```
                400                         405                         410
         TCC TTT ACC ATA AAG CCC GTG GGC TTC AAG GAC AGC CTG   1365
         Ser Phe Thr Ile Lys Pro Val Gly Phe Lys Asp Ser Leu
             415                 420                     425

ATC GTC CAG GTC ACC TTT GAT TGT GAC TGT GCC TGC CAG   1404
         Ile Val Gln Val Thr Phe Asp Cys Asp Cys Ala Cys Gln
                         430                 435

GCC CAA GCT GAA CCT AAT AGC CAT CGC TGC AAC AAT GGC   1443
         Ala Gln Ala Glu Pro Asn Ser His Arg Cys Asn Asn Gly
             440                 445                 450

AAT GGG ACC TTT GAG TGT GGG GTA TGC CGT TGT GGG CCT   1482
         Asn Gly Thr Phe Glu Cys Gly Val Cys Arg Cys Gly Pro
                         455                 460

GGC TGG CTG GGA TCC CAG TGT GAG TGC TCA GAG GAG GAC   1521
         Gly Trp Leu Gly Ser Gln Cys Glu Cys Ser Glu Glu Asp
         465                 470                 475

TAT CGC CCT TCC CAG CAG GAC GAG TGC AGC CCC CGA GAG   1560
         Tyr Arg Pro Ser Gln Gln Asp Glu Cys Ser Pro Arg Glu
                 480                 485                 490

GGT CAG CCC GTC TGC AGC CAG CGG GGC GAG TGC CTC TGT   1599
         Gly Gln Pro Val Cys Ser Gln Arg Gly Glu Cys Leu Cys
                         495                 500

GGT CAA TGT GTC TGC CAC AGC AGT GAC TTT GGC AAG ATC   1638
         Gly Gln Cys Val Cys His Ser Ser Asp Phe Gly Lys Ile
         505                 510                 515

ACG GGC AAG TAC TGC GAG TGT GAC GAC TTC TCC TGT GTC   1677
         Thr Gly Lys Tyr Cys Glu Cys Asp Asp Phe Ser Cys Val
                 520                 525

CGC TAC AAG GGG GAG ATG TGC TCA GGC CAT GGC CAG TGC   1716
         Arg Tyr Lys Gly Glu Met Cys Ser Gly His Gly Gln Cys
         530                 535                 540

AGC TGT GGG GAC TGC CTG TGT GAC TCC GAC TGG ACC GGC   1755
         Ser Cys Gly Asp Cys Leu Cys Asp Ser Asp Trp Thr Gly
                         545                 550             555

TAC TAC TGC AAC TGT ACC ACG CGT ACT GAC ACC TGC ATG   1794
         Tyr Tyr Cys Asn Cys Thr Thr Arg Thr Asp Thr Cys Met
                             560                 565

TCC AGC AAT GGG CTG CTG TGC AGC GGC CGC GGC AAG TGT   1833
         Ser Ser Asn Gly Leu Leu Cys Ser Gly Arg Gly Lys Cys
         570                     575                 580

GAA TGT GGC AGC TGT GTC TGT ATC CAG CCG GGC TCC TAT   1872
         Glu Cys Gly Ser Cys Val Cys Ile Gln Pro Gly Ser Tyr
                         585                 590

GGG GAC ACC TGT GAG AAG TGC CCC ACC TGC CCA GAT GCC   1911
         Gly Asp Thr Cys Glu Lys Cys Pro Thr Cys Pro Asp Ala
         595                 600                 605

TGC ACC TTT AAG AAA GAA TGT GTG GAG TGT AAG AAG TTT   1950
         Cys Thr Phe Lys Lys Glu Cys Val Glu Cys Lys Lys Phe
                     610                 615                 620

GAC CGG GAG CCC TAC ATG ACC GAA AAT ACC TGC AAC CGT   1989
         Asp Arg Glu Pro Tyr Met Thr Glu Asn Thr Cys Asn Arg
                             625                 630

TAC TGC CGT GAC GAG ATT GAG TCA GTG AAA GAG CTT AAG   2028
         Tyr Cys Arg Asp Glu Ile Glu Ser Val Lys Glu Leu Lys
             635                 640                 645

GAC ACT GGC AAG GAT GCA GTG AAT TGT ACC TAT AAG AAT   2067
         Asp Thr Gly Lys Asp Ala Val Asn Cys Thr Tyr Lys Asn
                         650                 655

GAG GAT GAC TGT GTC GTC AGA TTC CAG TAC TAT GAA GAT   2106
         Glu Asp Asp Cys Val Val Arg Phe Gln Tyr Tyr Glu Asp
```

```
                 660                           665                            670
TCT AGT GGA AAG TCC ATC CTG TAT GTG GTA GAA GAG CCA   2145
Ser Ser Gly Lys Ser Ile Leu Tyr Val Val Glu Glu Pro
        675                     680                     685

GAG TGT CCC AAG GGC CCT GAC T GAT GAGATCTAAG           2180
Glu Cys Pro Lys Gly Pro Asp
                690         692

CTT   2183
```

( 2 ) INFORMATION FOR SEQ ID NO:4:

( i ) SEQUENCE CHARACTERISTICS:
        ( A ) LENGTH: 718 amino acids
        ( B ) TYPE: Amino Acid
        ( D ) TOPOLOGY: Linear ( x i ) SEQUENCE DESCRIPTION: SEQ ID NO:4:

```
Met Arg Ala Arg Pro Arg Pro Arg Pro Leu Trp Ala Thr Val Leu
-26 -25                      -20                 -15

Ala Leu Gly Ala Leu Ala Gly Val Gly Val Gly Gly Pro Asn Ile
        -10              -5                       1

Cys Thr Thr Arg Gly Val Ser Ser Cys Gln Gln Cys Leu Ala Val
  5                  10                  15

Ser Pro Met Cys Ala Trp Cys Ser Asp Glu Ala Leu Pro Leu Gly
 20                  25                  30

Ser Pro Arg Cys Asp Leu Lys Glu Asn Leu Leu Lys Asp Asn Cys
 35                  40                  45

Ala Pro Glu Ser Ile Glu Phe Pro Val Ser Glu Ala Arg Val Leu
 50                  55                  60

Glu Asp Arg Pro Leu Ser Asp Lys Gly Ser Gly Asp Ser Ser Gln
 65                  70                  75

Val Thr Gln Val Ser Pro Gln Arg Ile Ala Leu Arg Leu Arg Pro
 80                  85                  90

Asp Asp Ser Lys Asn Phe Ser Ile Gln Val Arg Gln Val Glu Asp
 95                 100                 105

Tyr Pro Val Asp Ile Tyr Tyr Leu Met Asp Leu Ser Tyr Ser Met
110                 115                 120

Lys Asp Asp Leu Trp Ser Ile Gln Asn Leu Gly Thr Lys Leu Ala
125                 130                 135

Thr Gln Met Arg Lys Leu Thr Ser Asn Leu Arg Ile Gly Phe Gly
140                 145                 150

Ala Phe Val Asp Lys Pro Val Ser Pro Tyr Met Tyr Ile Ser Pro
155                 160                 165

Pro Glu Ala Leu Glu Asn Pro Cys Tyr Asp Met Lys Thr Thr Cys
170                 175                 180

Leu Pro Met Phe Gly Tyr Lys His Val Leu Thr Leu Thr Asp Gln
185                 190                 195

Val Thr Arg Phe Asn Glu Glu Val Lys Lys Gln Ser Val Ser Arg
200                 205                 210

Asn Arg Asp Ala Pro Glu Gly Gly Phe Asp Ala Ile Met Gln Ala
215                 220                 225

Thr Val Cys Asp Glu Lys Ile Gly Trp Arg Asn Asp Ala Ser His
230                 235                 240

Leu Leu Val Phe Thr Thr Asp Ala Lys Thr His Ile Ala Leu Asp
245                 250                 255

Gly Arg Leu Ala Gly Ile Val Gln Pro Asn Asp Gly Gln Cys His
```

| | | | | | | | | | | | |
|---|---|---|---|---|---|---|---|---|---|---|---|
| 260 | | | | | 265 | | | | 270 | | |
| Val | Gly | Ser | Asp | Asn | His | Tyr | Ser | Ala | Ser | Thr | Met | Asp | Tyr |
| 275 | | | | | 280 | | | | 285 | | |
| Pro | Ser | Leu | Gly | Leu | Met | Thr | Glu | Lys | Leu | Ser | Gln | Lys | Asn | Ile |
| 290 | | | | | 295 | | | | 300 | | |
| Asn | Leu | Ile | Phe | Ala | Val | Thr | Glu | Asn | Val | Val | Asn | Leu | Tyr | Gln |
| 305 | | | | | 310 | | | | 315 | | |
| Asn | Tyr | Ser | Glu | Leu | Ile | Pro | Gly | Thr | Thr | Val | Gly | Val | Leu | Ser |
| 320 | | | | | 325 | | | | 330 | | |
| Met | Asp | Ser | Ser | Asn | Val | Leu | Gln | Leu | Ile | Val | Asp | Ala | Tyr | Gly |
| 335 | | | | | 340 | | | | 345 | | |
| Lys | Ile | Arg | Ser | Lys | Val | Glu | Leu | Glu | Val | Arg | Asp | Leu | Pro | Glu |
| 350 | | | | | 355 | | | | 360 | | |
| Glu | Leu | Ser | Leu | Ser | Phe | Asn | Ala | Thr | Cys | Leu | Asn | Asn | Glu | Val |
| 365 | | | | | 370 | | | | 375 | | |
| Ile | Pro | Gly | Leu | Lys | Ser | Cys | Met | Gly | Leu | Lys | Ile | Gly | Asp | Thr |
| 380 | | | | | 385 | | | | 390 | | |
| Val | Ser | Phe | Ser | Ile | Glu | Ala | Lys | Val | Arg | Gly | Cys | Pro | Gln | Glu |
| 395 | | | | | 400 | | | | 405 | | |
| Lys | Glu | Lys | Ser | Phe | Thr | Ile | Lys | Pro | Val | Gly | Phe | Lys | Asp | Ser |
| 410 | | | | | 415 | | | | 420 | | |
| Leu | Ile | Val | Gln | Val | Thr | Phe | Asp | Cys | Asp | Cys | Ala | Cys | Gln | Ala |
| 425 | | | | | 430 | | | | 435 | | |
| Gln | Ala | Glu | Pro | Asn | Ser | His | Arg | Cys | Asn | Asn | Gly | Asn | Gly | Thr |
| 440 | | | | | 445 | | | | 450 | | |
| Phe | Glu | Cys | Gly | Val | Cys | Arg | Cys | Gly | Pro | Gly | Trp | Leu | Gly | Ser |
| 455 | | | | | 460 | | | | 465 | | |
| Gln | Cys | Glu | Cys | Ser | Glu | Glu | Asp | Tyr | Arg | Pro | Ser | Gln | Gln | Asp |
| 470 | | | | | 475 | | | | 480 | | |
| Glu | Cys | Ser | Pro | Arg | Glu | Gly | Gln | Pro | Val | Cys | Ser | Gln | Arg | Gly |
| 485 | | | | | 490 | | | | 495 | | |
| Glu | Cys | Leu | Cys | Gly | Gln | Cys | Val | Cys | His | Ser | Ser | Asp | Phe | Gly |
| 500 | | | | | 505 | | | | 510 | | |
| Lys | Ile | Thr | Gly | Lys | Tyr | Cys | Glu | Cys | Asp | Asp | Phe | Ser | Cys | Val |
| 515 | | | | | 520 | | | | 525 | | |
| Arg | Tyr | Lys | Gly | Glu | Met | Cys | Ser | Gly | His | Gly | Gln | Cys | Ser | Cys |
| 530 | | | | | 535 | | | | 540 | | |
| Gly | Asp | Cys | Leu | Cys | Asp | Ser | Asp | Trp | Thr | Gly | Tyr | Tyr | Cys | Asn |
| 545 | | | | | 550 | | | | 555 | | |
| Cys | Thr | Thr | Arg | Thr | Asp | Thr | Cys | Met | Ser | Ser | Asn | Gly | Leu | Leu |
| 560 | | | | | 565 | | | | 570 | | |
| Cys | Ser | Gly | Arg | Gly | Lys | Cys | Glu | Cys | Gly | Ser | Cys | Val | Cys | Ile |
| 575 | | | | | 580 | | | | 585 | | |
| Gln | Pro | Gly | Ser | Tyr | Gly | Asp | Thr | Cys | Glu | Lys | Cys | Pro | Thr | Cys |
| 590 | | | | | 595 | | | | 600 | | |
| Pro | Asp | Ala | Cys | Thr | Phe | Lys | Lys | Glu | Cys | Val | Glu | Cys | Lys | Lys |
| 605 | | | | | 610 | | | | 615 | | |
| Phe | Asp | Arg | Glu | Pro | Tyr | Met | Thr | Glu | Asn | Thr | Cys | Asn | Arg | Tyr |
| 620 | | | | | 625 | | | | 630 | | |
| Cys | Arg | Asp | Glu | Ile | Glu | Ser | Val | Lys | Glu | Leu | Lys | Asp | Thr | Gly |
| 635 | | | | | 640 | | | | 645 | | |
| Lys | Asp | Ala | Val | Asn | Cys | Thr | Tyr | Lys | Asn | Glu | Asp | Asp | Cys | Val |
| 650 | | | | | 655 | | | | 660 | | |

| Val | Arg | Phe | Gln | Tyr | Tyr | Glu | Asp | Ser | Ser | Gly | Lys | Ser | Ile | Leu |
| 665 |     |     |     |     | 670 |     |     |     | 675 |     |     |     |     |     |

| Tyr | Val | Val | Glu | Glu | Pro | Glu | Cys | Pro | Lys | Gly | Pro | Asp |
| 680 |     |     |     |     | 685 |     |     |     | 690 |     | 692 |     |

( 2 ) INFORMATION FOR SEQ ID NO:5:

( i ) SEQUENCE CHARACTERISTICS:
        ( A ) LENGTH: 100 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:5:

GAATTCTAGA GCCGCCATGA GAGCACGTCC TCGACCACGT CCTCTCTGGG 50

CGACTGTGCT GGCACTGGGA GCACTGGCTG GTGTTGGAGT AGGAGGGCCC 100

( 2 ) INFORMATION FOR SEQ ID NO:6:

( i ) SEQUENCE CHARACTERISTICS:
        ( A ) LENGTH: 104 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:6:

CGCCGCGGGA GGCGGACGAG ATGCGAGCGC GGCCGCGGCC CCGGCCGCTC 50

TGGGCGACTG TGCTGGCGCT GGGGCGCTG GCGGGCGTTG GCGTAGGAGG 100

GCCC 104

( 2 ) INFORMATION FOR SEQ ID NO:7:

( i ) SEQUENCE CHARACTERISTICS:
        ( A ) LENGTH: 4 amino acids
        ( B ) TYPE: Amino Acid
        ( D ) TOPOLOGY: Linear ( x i ) SEQUENCE DESCRIPTION: SEQ ID NO:7:

| Leu | Asn | Leu | Asp |
| 1   |     |     | 4   |

( 2 ) INFORMATION FOR SEQ ID NO:8:

( i ) SEQUENCE CHARACTERISTICS:
        ( A ) LENGTH: 39 base pairs
        ( B ) TYPE: Nucleic Acid
        ( C ) STRANDEDNESS: Double
        ( D ) TOPOLOGY: Linear ( x i ) SEQUENCE DESCRIPTION: SEQ ID NO:8:

CTGGCGGGCG TTGGCGTAGG AGGGCCCAAC ATCTGTACC 39

( 2 ) INFORMATION FOR SEQ ID NO:9:

( i ) SEQUENCE CHARACTERISTICS:
        ( A ) LENGTH: 98 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:9:

AATTCTAGAG CCGCCATGAG AGCACGTCCT CGACCACGTC CTCTCTGGGC 50

GACTGTGCTG GCACTGGGAG CACTGGCTGG TGTTGGAGTA GGAGGGCC 98

-continued ( 2 ) INFORMATION FOR SEQ ID NO:10:

( i ) SEQUENCE CHARACTERISTICS:
    ( A ) LENGTH: 90 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:10:

CTCCTACTCC AACACCAGCC AGTGCTCCCA GTGCCAGCAC AGTCGCCCAG 50

AGAGGACGTG GTCGAGGACG TGCTCTCATG GCGGCTCTAG 90

( 2 ) INFORMATION FOR SEQ ID NO:11:

( i ) SEQUENCE CHARACTERISTICS:
    ( A ) LENGTH: 9 amino acids
    ( B ) TYPE: Amino Acid
    ( D ) TOPOLOGY: Linear ( x i ) SEQUENCE DESCRIPTION: SEQ ID NO:11:

Leu Arg Ala Leu Glu Glu Arg Ala Ile
956      960      964

( 2 ) INFORMATION FOR SEQ ID NO:12:

( i ) SEQUENCE CHARACTERISTICS:
    ( A ) LENGTH: 27 base pairs
    ( B ) TYPE: Nucleic Acid
    ( C ) STRANDEDNESS: Double
    ( D ) TOPOLOGY: Linear ( x i ) SEQUENCE DESCRIPTION: SEQ ID NO:12:

CTCCGGGCCT TGGAGGAGAG GGCCATT 27

( 2 ) INFORMATION FOR SEQ ID NO:13:

( i ) SEQUENCE CHARACTERISTICS:
    ( A ) LENGTH: 20 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:13:

CTTGGAGGAG AGGTGATGAA 20

( 2 ) INFORMATION FOR SEQ ID NO:14:

( i ) SEQUENCE CHARACTERISTICS:
    ( A ) LENGTH: 20 base pairs
    ( B ) TYPE: Nucleic Acid
    ( C ) STRANDEDNESS: Single
    ( D ) TOPOLOGY: Linear ( x i ) SEQUENCE DESCRIPTION: SEQ ID NO:14:

AGCTTTCATC ACCTCTCCTC 20

( 2 ) INFORMATION FOR SEQ ID NO:15:

( i ) SEQUENCE CHARACTERISTICS:
    ( A ) LENGTH: 8 amino acids
    ( B ) TYPE: Amino Acid
    ( D ) TOPOLOGY: Linear ( x i ) SEQUENCE DESCRIPTION: SEQ ID NO:15:

Pro Lys Gly Pro Asp Ile Leu Leu
688   690        695

( 2 ) INFORMATION FOR SEQ ID NO:16:

( i ) SEQUENCE CHARACTERISTICS:
        ( A ) LENGTH: 24 base pairs
        ( B ) TYPE: Nucleic Acid
        ( C ) STRANDEDNESS: Double
        ( D ) TOPOLOGY: Linear ( x i ) SEQUENCE DESCRIPTION: SEQ ID NO:16:

CCCAAGGGCC CTGACATCCT GGTG    24

( 2 ) INFORMATION FOR SEQ ID NO:17:

( i ) SEQUENCE CHARACTERISTICS:
        ( A ) LENGTH: 17 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:17:

CTGACTGATG AGATCTA    17

( 2 ) INFORMATION FOR SEQ ID NO:18:

( i ) SEQUENCE CHARACTERISTICS:
        ( A ) LENGTH: 25 base pairs
        ( B ) TYPE: Nucleic Acid
        ( C ) STRANDEDNESS: Single
        ( D ) TOPOLOGY: Linear ( x i ) SEQUENCE DESCRIPTION: SEQ ID NO:18:

AGCTTAGATC TCATCAGTCA GGGCC    25

SOLUBLE ANALOGUES OF INTEGRINS

CROSS REFERENCES

This application is a divisional of U.S. application Ser. No. 08/380,227 filed 30 Jan. 1995, now abandoned, which application is a continuation of U.S. application Ser. No. 08/218,878 filed 28 Mar. 1994 (abandoned), which application is a continuation of U.S. application Ser. No. 07/821,337 filed 13 Jan. 1992 (abandoned), which application is a continuation of U.S. application Ser. No. 07/444,490 filed 1 Dec. 1989 (abandoned), which application is a continuation-in-part of U.S. application Ser. No. 07/290,224 filed 22 Dec. 1988 (abandoned), which applications are incorporated herein by reference and to which applications priority is claimed under 35 USC §120.

BACKGROUND OF THE INVENTION

This invention is concerned with the preparation of complex soluble receptors. In particular it is directed to the synthesis of recombinant receptors for cell matrix or plasma proteins.

Cellular membranes contain polypeptides which are lodged in the lipid bilayer. Such polypeptides contain a domain which anchors the protein in the cell membrane, a hydrophobic transmembrane domain, together in many instances with a C-terminal cytoplasmic sequence. In general, these polypeptides are single chain molecules or are multiple chain molecules derived from an ancestral single chain expression product by post-translational proteolytic processing. Such multiple chain polypeptides usually are covalently linked by disulfide bonds. However, some of these polypeptides are noncovalently associated with one another by salt bridges, Van der Waals forces, hydrophobic interactions and the like, and in such cases this association of polypeptide subunits into a larger aggregate is a prerequisite for biological activity.

The biological activity of such membrane-bound, multiple subunit molecules is varied, but in general reflects a receptor or binding function. Receptors serve to signal the cell regarding a condition or substance in the exterior environment of the cell, they serve to internalize an extracellular substance, or they function to attach cells to one another, to extracellular matrix substances, cell surface or plasma proteins.

A further subclass of membrane bound multiple subunit polypeptides are those in which each subunit is different, i.e. is not substantially homologous, and is encoded by a discrete gene. Such polypeptides are termed "MSP" (multiple subunit polypeptides) for the purposes of this invention. Numerous examples of such polypeptides or receptors are known, but the most substantial group is the class of cell surface receptors for extracellular matrix molecules, some of which have currently been identified and DNA encoding them cloned (see for example, Buck et al., "Ann. Rev. Cell Biol." 3:179 [1987] and Ruoslahti et al., "Science" 238:491 [1987].)

Of particular interest is the platelet glycoprotein IIb-IIIa, a platelet membrane-bound receptor involved in platelet aggregation and which binds to fibrinogen, fibronectin, vitronectin and von Willebrand factor. The two subunits constituting this receptor have been cloned (Fitzgerald et al. "Biochemistry" 26:8158 [1987] and Fitzgerald et al. "J. Biol. Chem." 262(9):3936 [1987]). Bennett et al. reported expression of the GPIIb subunit in Cos-1 cells, but the subunit was not found on the cell membrane (AHA 61st Scientific Sessions, Nov. 15, 1988). Bennett et al. suggested that membrane localization might require the formation of the IIb-IIIa complex. There was no teaching or suggestion that a recombinant, membrane-bound GPIIb-IIIa, even if it could be made, would bind to its proper ligands, e.g., fibrinogen. In addition, an oral disclosure by Frelinger et al. at the same meeting purported to describe the transient expression of full length GPIIb-IIIa on an unidentified recombinant cell surface; no other information was provided relating to the manner in which expression was allegedly obtained.

Corbi et al. orally reported the transient expression of functional full length LFA-1 in COS cells in September 1988 at the Titisee Symposium sponsored by Boehringer Ingelheim.

Membrane-bound MSPs present difficulties in purification and stability since the hydrophobic domains tend to induce the MSPs to micelles or aggregates. A form of these receptors is needed that is soluble, particularly in body fluids such as blood and in pharmacological excipients such as saline, without forming multiple molecular aggregates beyond proper heterodimer assembly. Accordingly, it is an object herein to synthesize such MSP forms.

It is another object to produce soluble forms of the GPIIb-IIIa receptor which are capable of properly binding their normal ligands.

It is a further object to express GPIIIa in recombinant cell culture.

It is an additional object to produce high yields of GPIIb-IIIa from recombinant cell culture.

These and other objects will be apparent from consideration of this application as a whole.

SUMMARY

In accordance with this invention, a method is provided for the preparation of a secreted analogue of a cell membrane-bound multiple subunit polypeptide (MSP), each subunit of which is encoded by a discrete gene, comprising 1) introducing into the nucleic acid encoding each of the subunits a mutation encoding an amino acid sequence variant of the MSP that renders the MSP no longer capable of becoming lodged in a lipid bilayer, and 2) transfecting a host cell with the nucleic acid of step 1, 3) culturing the host cell of step 2 and 4) recovering from the host cell culture biologically active soluble MSP. Also in accordance with this invention, nucleic acid and expression vectors are provided which encode an amino acid sequence variant of an integrin chain, in particular a variant in which the transmembrane domain of the integrin chain is modified so that it is no longer capable of becoming lodged in the cell membrane.

Also provided is a method for the preparation of GPIIb-IIIa comprising transforming a permissive host cell with nucleic acid encoding GPIIb-IIIa and culturing the host cell until GPIIb-IIIa accumulates in the cell membrane.

In specific embodiments, the objects of this invention are accomplished by providing a biologically active MSP amino acid sequence variant selected from the group consisting of (a) an MSP amino acid sequence variant having an inactivated membrane anchor domain and (b) a polypeptide comprising an MSP extracellular domain fused to the sequence of a polypeptide which is different from the MSP, this latter, for example, selected from an immunogen or a protein with a long plasma half life such as an immunoglobulin constant domain.

In another embodiment, MSP amino acid residues or carbohydrate substituents of HSPs or HSP analogues otherwise described herein are derivatized by covalent modification or are conjugated to nonproteinaceous polymers such as polyethylene glycol to produce an MSP derivative which exhibits improved circulatory half life.

In particular embodiments a polypeptide comprising a biologically active extracellular domain of an integrin is fused at its C-terminus to an immunoglobulin constant domain, or is linked to an immunogenic polypeptide.

The MSP variants provided herein are purified and formulated in pharmacologically acceptable vehicles for diagnostic or preparatory utility or in vivo use in the modulation of cell adhesion.

BRIEF DESCRIPTION OF THE DRAWINGS

Figure 1A:
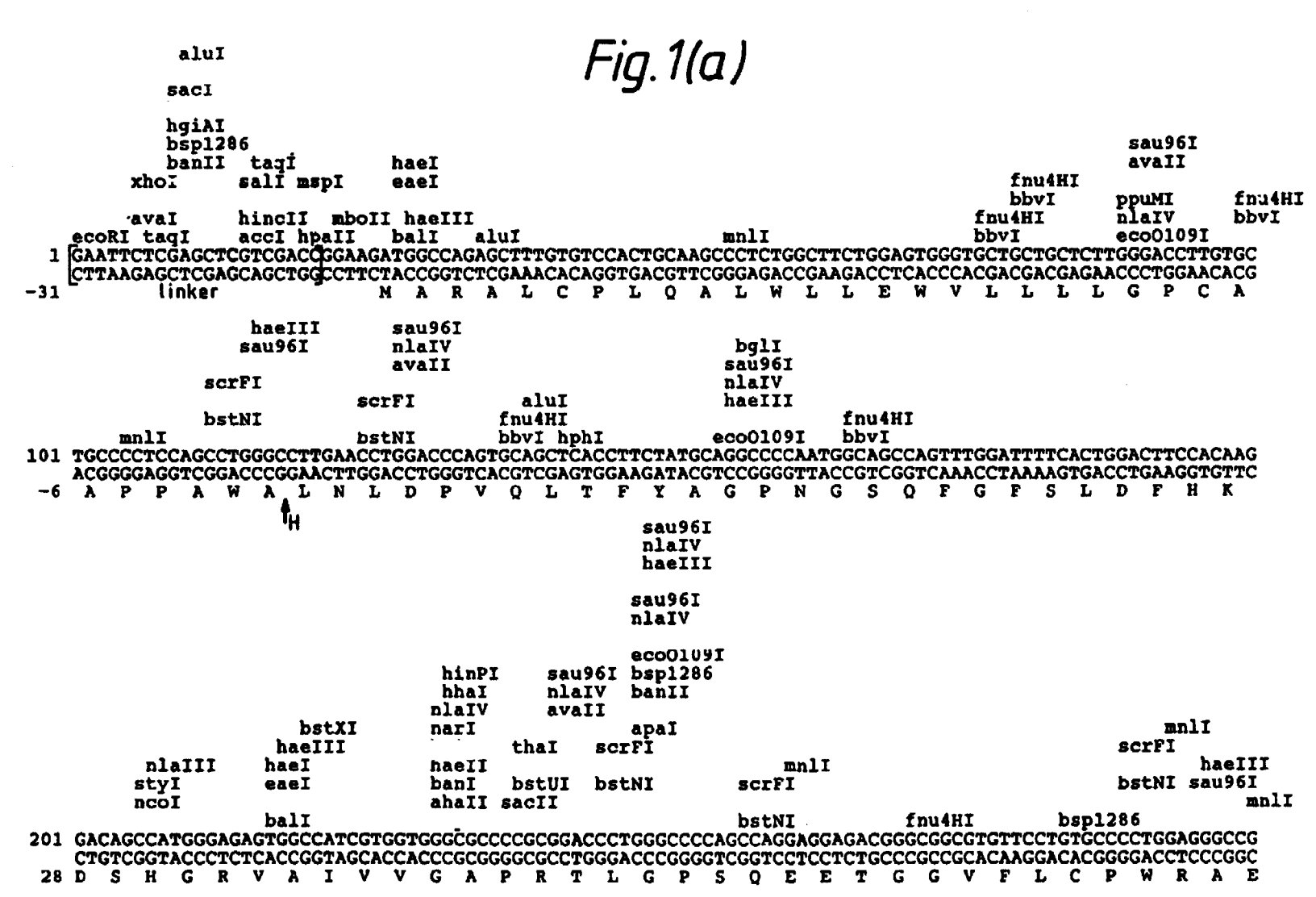
Figure 1B:
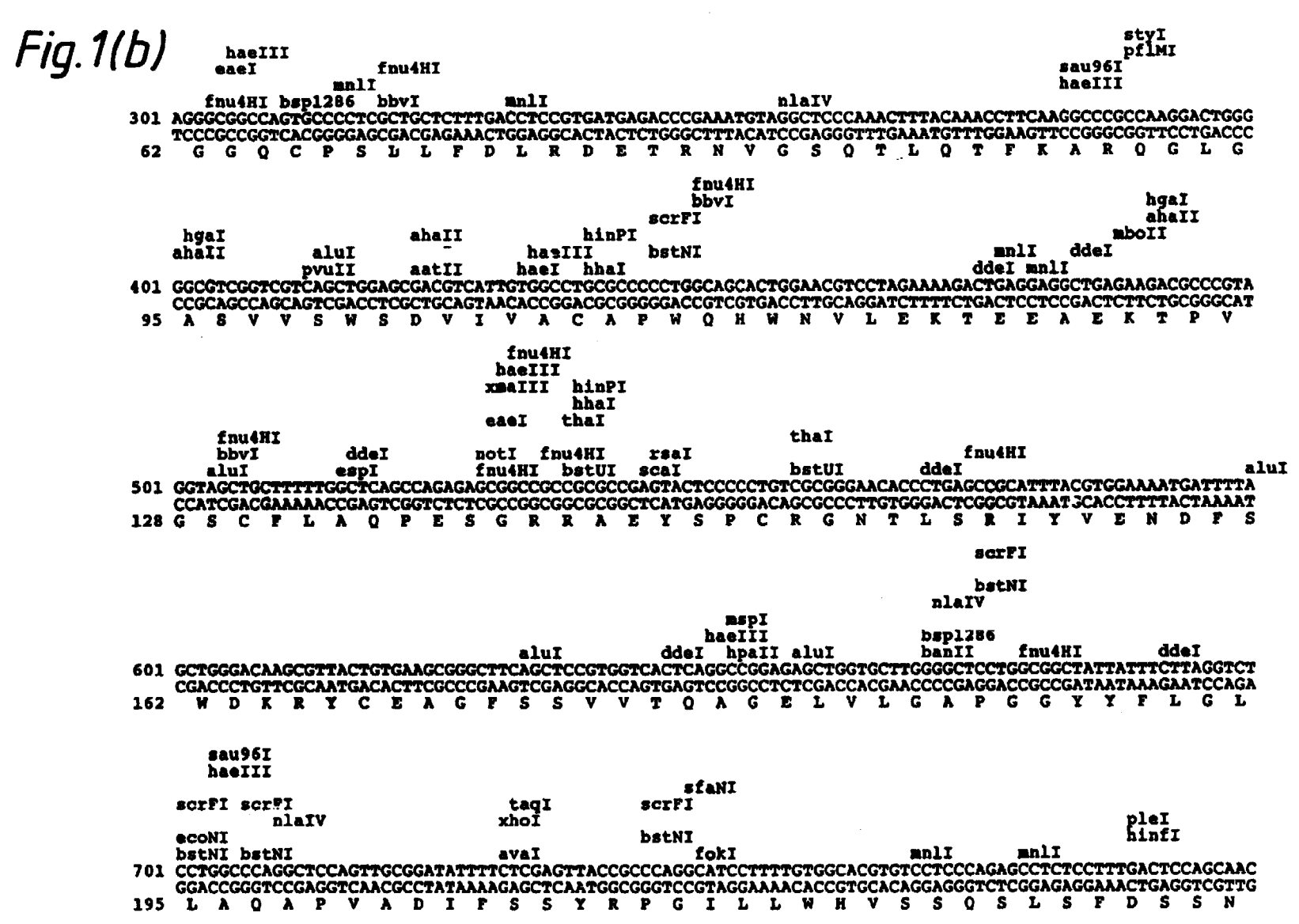
Figure 1F:
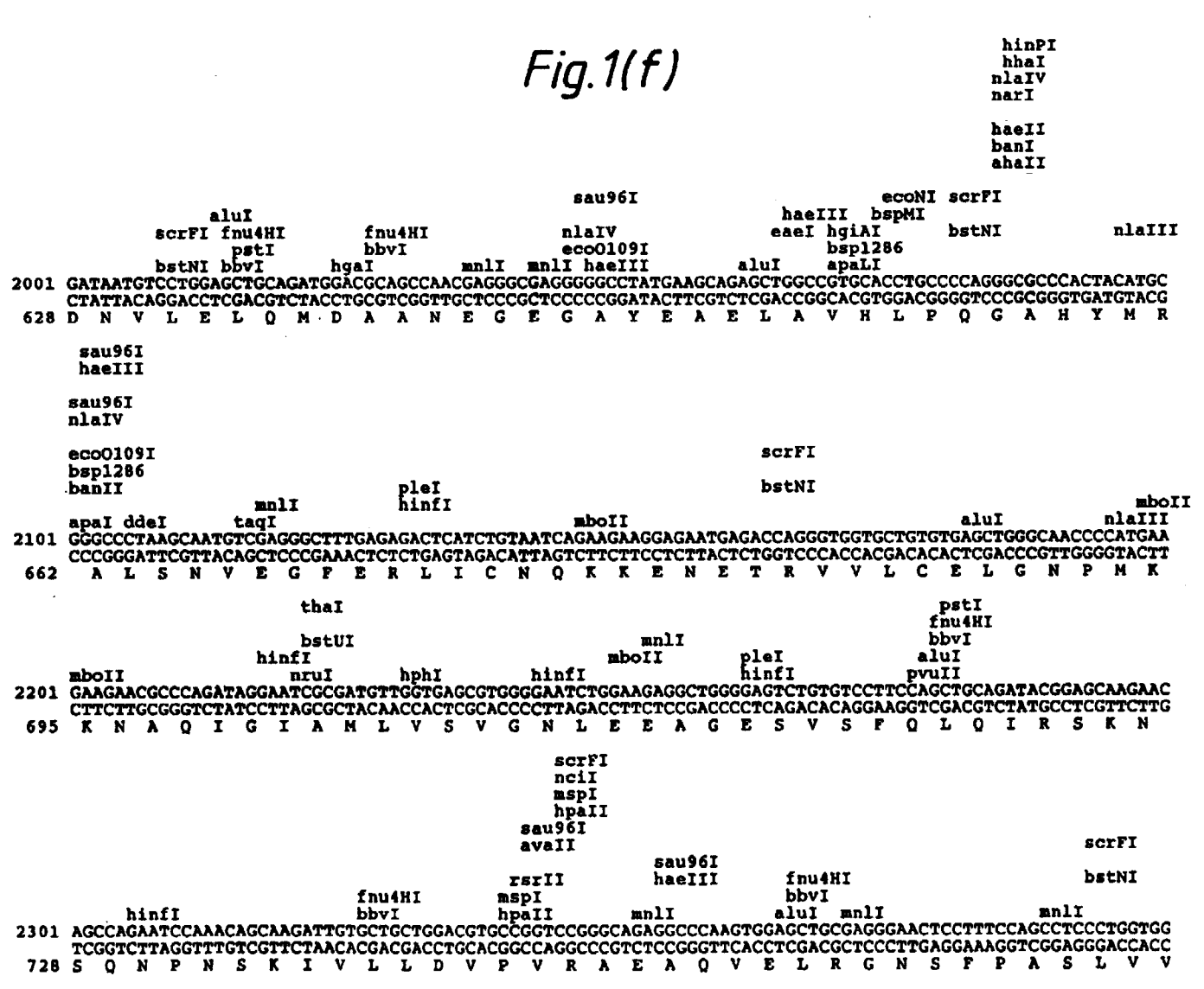

FIGS. 1(a)–1(k) depict the amino acid SEQ ID NO:2 and nucleotide sequence SEQ ID NO:1 of a secreted form of the GPIIb subunit of the MSP CPIIb-IIIa. The signal processing site for the heavy and light forms of this subunit are designated, respectively, with arrow-H and arrow-L.

Figure 2A:
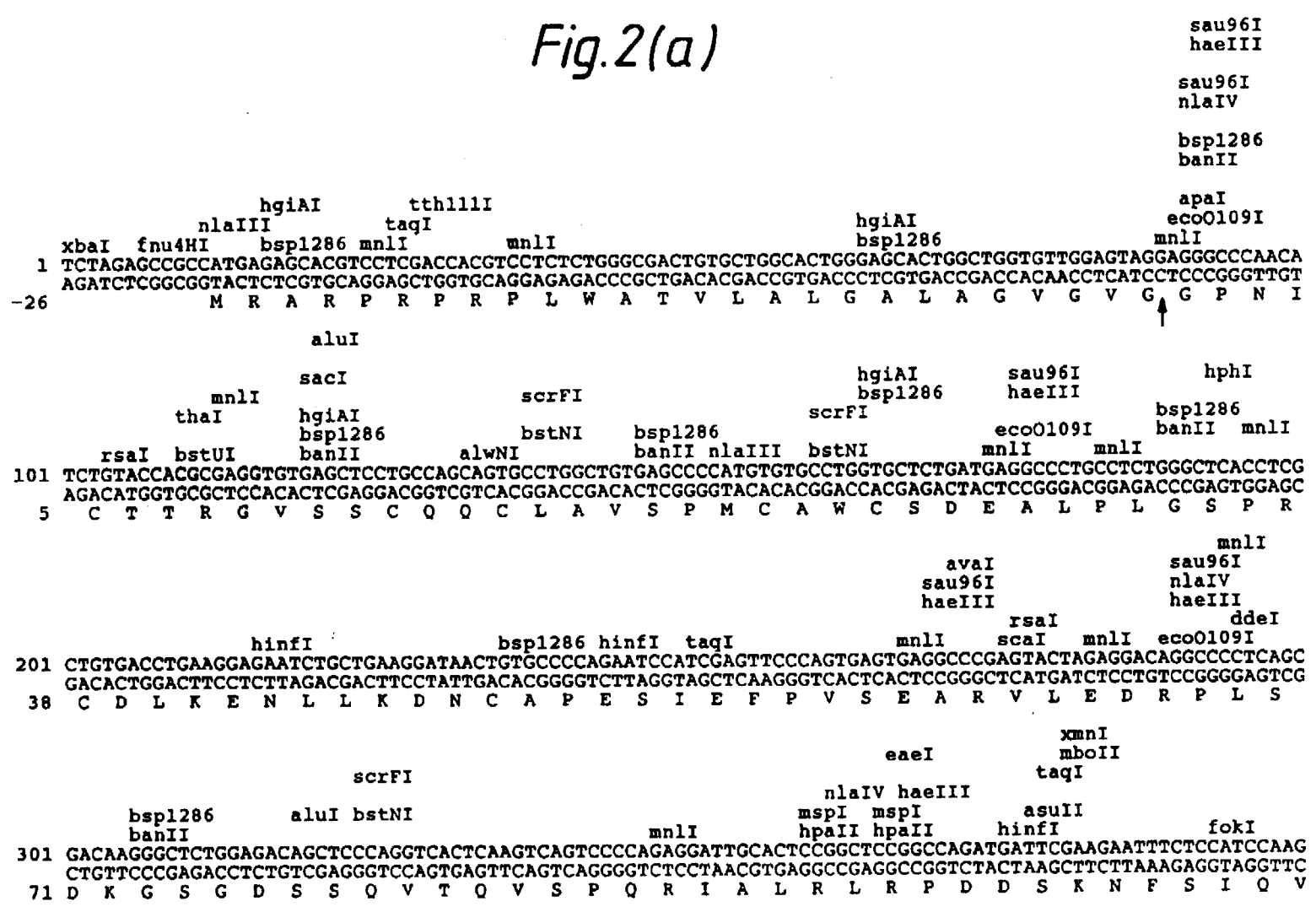
Figure 2B:
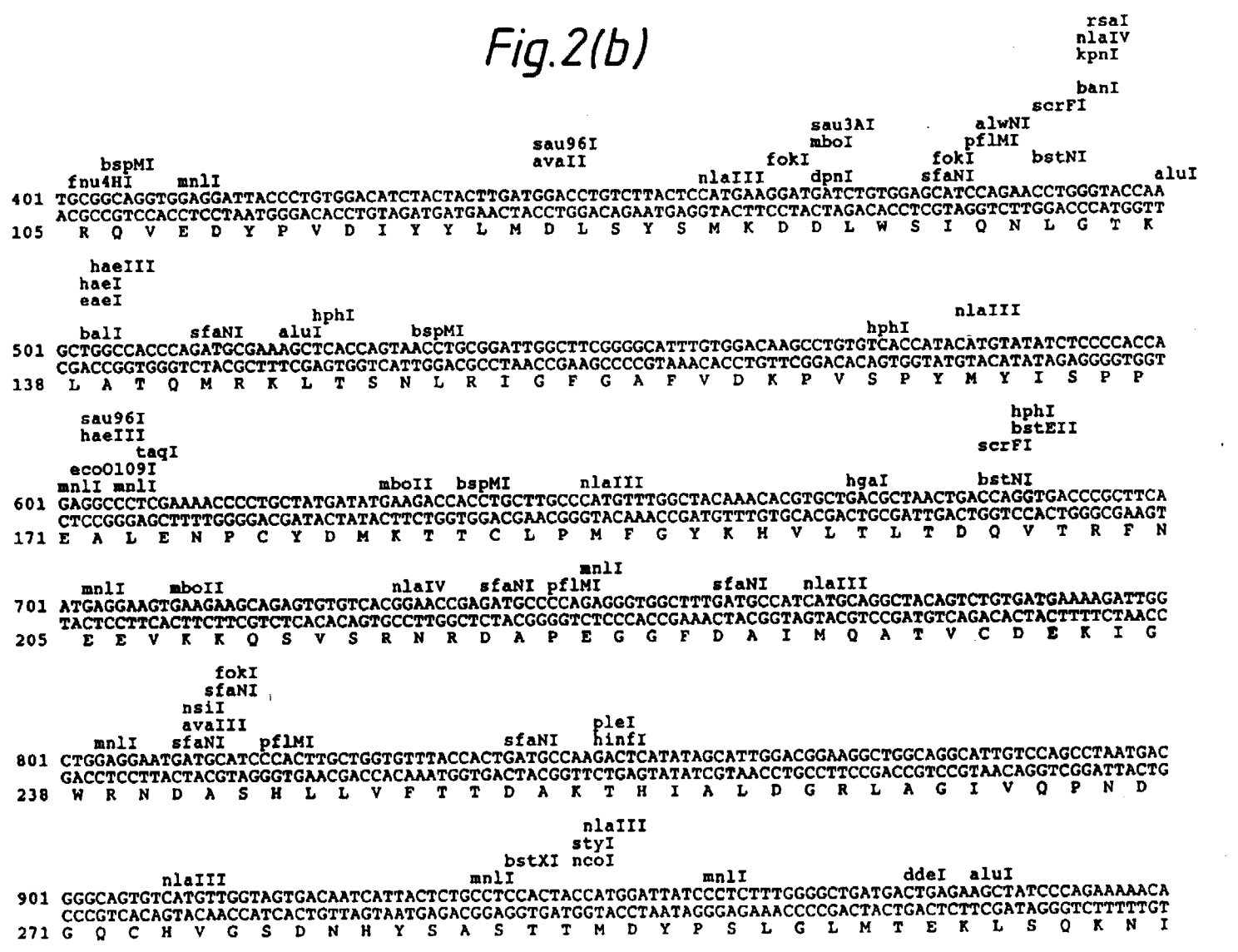

FIGS. 2(a)–2(e) depict the amino acid SEQ ID NO:4 and nucleotide sequence SEQ ID NO:3 of a secreted form of the GPIIIa subunit of the MSP CPIIb-IIIa. The signal processing site is designated with an arrow.

FIG. 3 depicts a comparison of the native natural SEQ ID NO:6 and redesigned synthetic SEQ ID NO:5 nucleic acid sequences at the 5' end of the GPIIIa gene Residues-26 through 27SEQ ID NO.2.

DETAILED DESCRIPTION

An MSP is defined herein to be a multichain polypeptide, at least one chain of which is ordinarily anchored in a cell membrane and at least two chains of which are discretely encoded. MSPs ordinarily contain at least two distinct chains, two of which are lodged directly in the cell membrane. One or more additional chains maybe covalently or noncovalently bound to the MSP chains ordinarily lodged in the cell membrane, but the additional chains may not themselves be anchored in the membrane. Such chains typically result from the post-translational processing of a single chain that becomes membrane anchored. Discretely encoded subunits are those which do not result from the post-translational processing of a single translated protein, and their amino acid sequences are not homologous (i.e. the sequences of the subunits are not the same, and they do not assemble in nature into dimers or multimers of the same polypeptide). Instead, they are produced by the translation of independent mRNAs or polycistronic messages. Thus, the nucleic acids encoding MSP polypeptides ordinarily are found in nature under the control of different promoters and other transcription control sequences.

MSPs include principally cell surface receptors for extracellular matrix molecules, also defined as cellular adhesion receptors. Many of these receptors and their ligands, such ligands including the extracellular matrix molecules and plasma proteins such as fibrinogen as well as cell surface proteins such as I-CAM, are central to cellular adhesion phenomena involved in wound healing, morphogenic mobility, developmentally unrelated cellular migrations, hemostasis and metastasis. These cellular adhesion receptors are identified by functional and structural features. Functionally, they typically bind to polypeptides incorporating the sequence RGD, from which they are dissociated by competition with other polypeptides containing the RGD sequence such as the peptides RGDS or RGDV. Also, they frequently require a divalent cation such as calcium for ligand binding. MSPs may or may not include members of the immunoglobulin superfamily such as the T cell receptor. A group of MSPs involved in cell surface intracellular adhesive interactions have been designated integrins (see Buck et al., "Ann. Rev. Cell Biol." 3:179–205 [1987]).

Structurally, such cellular adhesion receptors belong to a supergene family of multimers in which a first single-chain polypeptide or disulfide cross-linked multi-chain polypeptide ($\alpha$-chain) is noncovalently associated with a second and different polypeptide (designated a $\beta$-chain), thereby forming a heteromultimer. The $\alpha$-chains of these receptors are quite diverse in terms of their amino acid sequence, and include the $\alpha$ subunit of avian integrin (band 1); $\alpha_1$, $\alpha_2$, and $\alpha_4$ of VLA 1, 2 and 4; $\alpha_3$ of VLA 3 and arian integrin (band 2); $\alpha_F$ of VLA 5 and the fibronectin receptor; $\alpha_L$ of LFA-1; $\alpha_M$ of Mac-1; $\alpha_X$ of p150,95; $\alpha_H \alpha_L$ of GPIIb; and $\alpha_V$ of vitronectin. The $\beta$-chains typically fall into three classes, $\beta_1$ (avian integrin [band 3]; fibronectin receptor and VIA), $\beta_2$ (LFA-1/Mac-1; p150,95) and $\beta_3$ (GPIIb-IIIa and vitronectin receptor), the members of each $\beta$-class being substantially homologous or identical. It is preferred that the MSP selected contain the two (or more) chains which ordinarily associate with one another in nature since non-naturally occurring heteromers may not form complexes.

Each chain of an MSP is expressed in its native environment as a preprotein comprising a secretion signal which is processed during the extracellular orientation of the receptor. Also, at least one chain of each subunit will have a hydrophobic anchor containing a polypeptide sequence serving as a site for covalent addition of lipid, phospholipid, or a domain located in the C-terminal portion of the polypeptide and containing about from 10 to 30 predominantly hydrophobic residues such as phe, leu, ile, val, met, gly and ala. Such membrane anchoring sequences or domains will be collectively referred to herein as membrane anchor domains. A short hydrophilic cytoplasmic domain, on the order of 10 to 100 residues, usually is found C-terminal to transmembrane domains. The term subunit should be understood to mean polypeptide chain; it does not refer to domains or functional subregions of a given polypeptide chain.

Certain MSPs share other structural features, for example, wherein one subunit of the receptor contains cysteine-rich tandem amino acid sequence repeats in which greater than about 80% of the cysteine residues are alignable within about two residues of the cysteine residues of the tandem repeats of GPIIIa, wherein one subunit has the consensus N-terminal sequence Tyr/Phe/Leu-Asn-Leu-Asp SEQ ID NO.7, or one subunit contains an amino acid domain having substantial sequence homology to the calmodulin calcium binding site.

Also included within the scope of MSPs are those receptors which are homologous to the above-described members of the integrin superfamily. Homologous, as defined herein, means having the sequence of a polypeptide of a member of the integrin superfamily which at least has substantially the same amino acid sequence homology to a known member of the superfamily as any presently known member has to any other known member. Typically, homologous means having greater than about 40% amino acid homology after aligning sequences for maximum homology, but not taking into account conservative substitutions.

This invention in part is based upon the discovery that discretely encoded MSPs, when modified to eliminate their ability to insert into the host cell membrane, nonetheless are fully assembled and secreted in biologically active form by recombinant host cells. Recombinant host cells secrete the subunits in correct association with one another such that the assembly exhibits the biological activity of the extracellular domain of the native MSP, despite the fact that proper association of the subunits is no longer facilitated by juxtaposition in the cell membrane. Further, proper assembly has been obtained even when the MSP sequences have not been fused to multimer-forming polypeptides, i.e. it has been found that MSPs will properly associate even without the aid of extraneous cross-linking polypeptides such as immunoglobulin chains.

Biological activity is defined in terms of the ability of the secreted MSP to qualitatively bind the ligand ordinarily bound by the MSP in its native environment, although it will be appreciated that the kinetics or other quantitative characteristics of ligand binding by the secreted MSP may vary from those of the native cell bound MSP. While secreted MSP most likely will retain many functional immune epitopes capable of cross-reacting with antibody raised against the native MSP, this alone is not enough for the secreted MSP to exhibit biological activity as defined herein; "biologically active" secreted MSP must exhibit the ability to bind to its ligand as well. However, it will be understood that not all MSP produced in accord with this invention need to exhibit biological activity in the sense defined here. Such biologically inactive but, for example, immunologically active MSP analogues find use in diagnostic assays, in raising antibodies against MSP, or in the purification of antibodies to MSP.

This invention is particularly concerned with amino acid sequence variants of MSPs. Amino acid sequence variants of MSPs are prepared with various objectives in mind, including increasing the affinity of the MSP for its binding partner, facilitating the stability, purification and preparation of the MSP (including enhanced water solubility and reduced membrane affinity), increasing its plasma half life, improving therapeutic efficacy as described above, introducing additional functionalities and lessening the severity or occurrence of side effects during therapeutic use of the MSP. Amino acid sequence variants of MSPs fall into one or a combination of the following classes: insertional, substitutional or deletional variants. Each MSP variant or analogue will have one inactivated membrane anchor domain, and this will be accomplished by insertion, substitution or deletion, but these variants optionally comprise additional mutations that are involved in other than inactivating the membrane anchor domain of one chain of the native MSP.

Insertional amino acid sequence variants are those in which one or more amino acid residues extraneous to the MSP are introduced into a predetermined site in the MSP including the C or N termini. Such variants are referred to as fusions of the MSP and a polypeptide containing a sequence which is other than that which is normally found in the MSP at the inserted position. Several groups of fusions are contemplated herein.

Immunologically active MSP fusions comprise an MSP and a polypeptide containing a non-MSP epitope. The non-MSP epitope is any immunologically competent polypeptide, i.e., any polypeptide which is capable of eliciting an immune response in the animal to which the fusion is to be administered or which is capable of being bound by an antibody raised against the non-MSP polypeptide. Typical non-MSP epitopes will be those which are borne by allergens, autoimmune epitopes, or other potent immunogens or antigens recognized by pre-existing antibodies in the fusion recipient, including bacterial polypeptides such as trpLE, beta-galactosidase, viral polypeptides such as herpes gD protein, and the like. Immunogenic fusions are produced by cross-linking in vitro or by recombinant cell culture transformed with DNA encoding an immunogenic polypeptide. It is preferable that the immunogenic fusion be one in which the immunogenic sequence is joined to or inserted into the MSP or fragment thereof by a peptide bond(s). These products therefore consist of a linear polypeptide chain containing MSP epitopes and at least one epitope foreign to the MSP. It will be understood that it is within the scope of this invention to introduce the epitopes anywhere within the MSP molecule or fragment thereof. Such fusions are conveniently made in recombinant host cells or by the use of bifunctional cross-linking agents. The use of a cross-linking agent to fuse the MSP to the immunogenic polypeptide is not as desirable as a linear fusion because the cross-linked products are not as easily synthesized in structurally homogeneous form.

These immunogenic insertions are particularly useful when formulated into a pharmacologically acceptable carrier and administered to a subject in order to raise antibodies against the MSP, which antibodies in turn are useful in diagnostics or in purification of MSP by immunoaffinity techniques known per se. Alternatively, in the purification of MSPs, binding partners for the fused non-MSP polypeptide, e.g. antibodies, receptors or ligands, are used to adsorb the fusion from impure admixtures, after which the fusion is eluted and, if desired, the MSP is recovered from the fusion, e.g. by enzymatic cleavage.

Other fusions, which may or may not also be immunologically active, include fusions of the mature MSP sequence with a signal sequence heterologous of the MSP, fusions of transmembrane-modified MSPs (including sequence deletions or modifications so that the MSP could not lodge in the cell membrane), for example, to polypeptides having enhanced plasma half life (ordinarily >about 20 hours) such as immunoglobulin chains or fragments thereof which confer enhanced plasma half life.

Signal sequence fusions are employed in order to more expeditiously direct the secretion of the MSP. The heterologous signal sequence replaces the native MSP signal, and when the resulting fusion is recognized, i.e. processed and cleaved by the host cell, the MSP is secreted. Signals are selected based on the intended host cell, and may include bacterial yeast, mammalian and viral sequences. The native MSP signal or the herpes gD glycoprotein signal is suitable for use in mammalian expression systems.

Plasma proteins which have enhanced plasma half-life longer than that of soluble forms of MSPs having modified membrane anchor domains include serum albumin, immunoglobulins, apolipoproteins, and transferrin. Preferably, the MSP-plasma protein used for the fusion is not significantly immunogenic in the animal in which it is used (i.e., it is homologous to the therapeutic target) and the plasma protein does not cause undesirable side effects in patients by virtue of its normal biological activity.

In a specific embodiment the MSP extracellular domain is conjugated with an immunoglobulin constant region sequence. Immunoglobulins and certain variants thereof are known and many have been prepared in recombinant cell culture. For example, see U.S. Pat. No. 4,745,055; EP 256,654; Faulkner et al., Nature 298:286 (1982); EP 120,694; EP 125,023; Morrison, J. Immun. 123:793 (1979); Kohler et al., P.N.A.S. USA 77:2197 (1980); Raso et al., Cancer Res. 41:2073 (1981); Morrison et al., Ann. Rev. Immunol. 2:239 (1984); Morrison, Science 229:1202 (1985); Morrison et al., P.N.A.S. USA 81:6851 (1984); EP 255,694; EP 266,663; and WO 88/03559. Reassorted immunoglobulin chains also are known. See for example U.S. Pat. No. 4,444,878; WO 88/03565; and EP 68,763 and references cited therein. See also Gascoigne et al., P.N.A.S. USA 84:2936-2940 (May, 1987), EP 325,224, and Thesis of Andrew Scott Peterson (Harvard University; degree awarded Nov. 22, 1988).

Ordinarily, the extracellular domains of MSPs are fused C-terminally to the N-terminus of the constant region of an immunoglobulin in place of the variable region(s) thereof, retaining at least functionally active hinge, CH2 and CH3 domains of the constant region of an immunoglobulin heavy chain. Two forms of such fusions are embraced herein. In one, the extracellular domains of two or more ordinarily membrane-bound MSP chains are fused N or C terminally to immunoglobulin constant regions (heterofusion), while in the other form only one chain of the MSP is fused to a constant region (monofusion). The heterofusions include fusions with either light or heavy chain constant regions, or both. The heterofusion is produced by transforming a host cell with DNA encoding the light chain fusions, the heavy chain fusions or both. For example, transfection with DNA encoding one MSP chain fused to a heavy chain constant region and the other MSP chain fused to a light chain constant region will result in heterotetramers or heterodimers bearing light and heavy chain fusions with MSP chains. These are not as desirable as monofusions since they are not as likely to be biologically active. Note that monofusions may contain more than one fused chain, but in these cases the MSP chain will always originate with the same subunit.

Monofusions are immunoglobulin variants in which one chain of an MSP is fused to a heavy or light chain (or constant domain thereof), while the remaining chain(s) of the MSP are not fused to an immunoglobulin but rather are associated with the fused chain in substantially the fashion as is normally the case with the native MSP. Typically, both the fused and unfused MSP chains in monofusions will be variants in which the membrane anchor domains are modified so as to not lodge in the membrane, most commonly where the membrane anchor domain of one MSP chain is deleted, and in the other the membrane anchor domain is deleted and then the remaining extracellular region fused at its N-terminus to the C-terminus of an immunoglobulin constant domain. The MSP chain or its fragment is fused to either a light chain or a heavy chain, but preferably a heavy chain. If the MSP only contained one membrane anchored chain then the remaining chain(s) will typically have their native sequence.

It may be desirable to produce mono-or polyfusions having immunoglobulin antigen binding capability as well as the capacity to bind the MSP ligand. Such products are made by transforming the host cells with DNA encoding light and heavy chain capable of binding an antigen (or are selected to already produce light chain) together with the light and/or heavy chain MSP fusion and the unfused MSP chain(s) (in the case of monofusions). This will yield constructs, for example, having the normal structures of immunoglobulins except that one or both light-heavy arms of the immunoglobulin will comprise a fusion with one chain of the MSP which in turn is assembled (covalently or noncovalently) with the remaining chain(s) of the MSP.

In those instances in which the fusion transformants also produce (or are transformed to produce) immunoglobulin chains not fused to an MSP subunit, the immunoglobulin variable domains may have unknown or known specificity for a given antigen. It is preferred that the host cells not be constitutively capable of making undetermined antibody, but rather that if they are to produce antibody that it be by transformation with DNA encoding a known immunoglobulin. Such immunoglobulins (which may include both heavy as well as light chains) exhibit specificity for a known antigen. Alternatively, these companion immunoglobulin chains will be devoid of functional variable or hypervariable domains (so as to be capable of multimer assembly but not antigen binding activity). For example, a product MSP fusion secreted and recoverable from host cells capable of expressing an intact heavy and light chain companion immunoglobulin will bear an antigen binding functionality as well as an MSP functionality. Such products will facilitate the crosslinking of MSP ligand with any desired antigen. Host cells may make more than one immunoglobulin product in such multiple transformations, and accordingly it may be necessary to recover one multimer form from another. This, however, will be a routine matter requiring separation on a gel or other chromatographic procedure, or by affinity chromatography based on the MSP ligand, the antigen or both.

Other proteins having extended plasma half life are fused to the MSP in similar fashion, except that instead of an immunoglobulin chain a transferrin, albumin, apolipoprotein or other sequence is employed. Monofusions are preferred when MSP chains are fused to single chain plasma proteins which do not ordinarily assemble into multimers.

The boundary for an MSP extracellular domain generally is at, or within about 20 residues N-terminal from, the N-terminus of the membrane anchor domain, and are readily identified from an inspection of the MSP sequence. It is not necessary to use the entire MSP extracellular domain, however, since smaller segments are commonly found to be adequate for ligand binding. Such segments are routinely identified by making deletional mutants or enzymatic digests and screening for ligand binding to identify active fragments, and fall within the scope of the term "MSP".

The MSP extracellular domain generally is fused at its C-terminus to the N-terminus of the immunoglobulin constant region or other stable plasma protein. The precise site at which the fusion is made is not critical; other sites neighboring or within the extracellular region or C-terminal to the mature N-terminus of the plasma protein may be selected in order to optimize the secretion or binding characteristics of the soluble MSP. The optimal site will be determined by routine experimentation.

Exemplary hetero-and chimeric MSP-immunoglobulin variants produced in accordance with this invention are schematically diagrammed below. "A" means at least a portion of the extracellular domain of an MSP containing its ligand binding site; $A_1$, $A_2$, $A_3$, etc. represent individual subunit chains of A; $V_L$, $V_H$, $C_L$ and $C_H$ represent light or heavy chain variable or constant domains of an immunoglobulin; n is an integer; and Y designates a covalent cross-linking moiety.

(a) $AC_L$;

(b) $AC_L$-$AC_L$;

(c) $AC_H$-[$AC_H$, $AC_L$-$AC_H$, $AC_L$-$V_H C_H$, $V_L C_L$-$AC_H$, or $V_L C_L$-$V_H C_H$];

(d) $AC_L$-$AC_H$- [$AC_H$, $AC_L$-$AC_H$, $AC_L$-$V_H C_H$, $V_L C_L$-$AC_H$, or $V_L C_L$-$V_H C_H$];

(e) $AC_L$-$V_H C_H$-[$AC_H$, $AC_L$-$AC_H$, $AC_L$-$V_H C_H$, $V_L C_L$-$AC_H$, or $V_L C_L$-$V_H C_H$];

(f) $V_L C_L$-$AC_H$-[$AC_H$, $AC_L$-$AC_H$, $AC_L$-$V_H C_H$, $V_L C_L$-$AC_H$, or $V_L C_L$-$V_H C_H$]; or (g) [A-Y]$_n$- [$V_L C_L$-$V_H C_H$]$_2$.

The structures shown in this table show only key features, e.g. they do not show disulfide bonds. These are omitted in the interests of brevity. However, where such domains are required for binding activity they shall be construed as being present in the ordinary locations which they occupy in the immunoglobulin domain. These examples are representative of divalent antibodies; more complex structures would result by employing immunoglobulin heavy chain sequences from other classes, e.g. IgM. The immunoglobulin $V_L V_H$ antibody combining site, also designated as the companion immunoglobulin, preferably is capable of binding to a predetermined antigen.

Exemplary immunoglobulin constructs are described schematically below. Vertical lines indicate a noncovalent or covalent associative relationship.

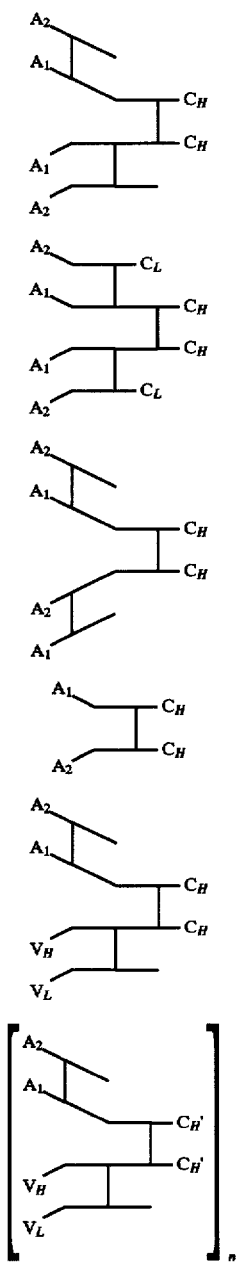

where n = 5 and $C_H'$ is the secreted heavy chain of IgM

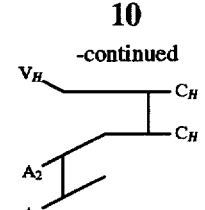

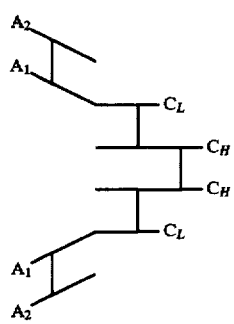

In product "(o)" the $C_H$ V domains have been deleted.

Suitable companion immunoglobulin combining sites and fusion partners are obtained from human IgG-1, -2, -3, or -4 subtypes, IgA, IgE, IgD or IgM, but preferably IgG-1. It is preferred to use the soluble form of IgM, or one in which the IgM membrane anchor domain has been modified so that it no longer lodges in the membrane.

A preferred embodiment is a fusion of an N-terminal portion of an MSP with a sequence beginning in the hinge region just upstream of the papain cleavage site which defines IgG $F_c$ chemically (residue 216, taking the first residue of heavy chain constant region to be 114 [Kabat et al., "Sequences of Proteins of Immunological Interest" 4th Ed., 1987], or analogous sites of other immunoglobulins).

The immunoglobulin or other plasma-stable polypeptide is fused to the C-termini of one or more of the MSP subunits, typically in place of at least one transmembrane and cytoplasmic domain of an MSP chain, although ordinarily only one of the subunits is substituted. In the case of GPIIb-IIIa this would be the beta subunit. The immunoglobulin domain such as a heavy chain also can be associated in normal fashion with a truncated or intact immunoglobulin heavy chain.

Variants in which an MSP extracellular domain is substituted for the variable region of an immunoglobulin chain are believed to exhibit improved in vivo plasma half life. These chimeras are constructed in a fashion similar to chimeric antibodies in which a variable domain from an antibody of one species is substituted for the variable domain of another species. See, for example, EP 0 125 023; Munro, Nature 312:(13 Dec. 1984); Neuberger et al., Nature 312: (13 Dec. 1984); Sharon et al., Nature 309: (24 May 1984); Morrison et al., Proc. Natl. Acad. Sci. USA 81:6851–6855 (1984); Morrison et al. Science 229:1202–1207 (1985); and Boulianne et al., Nature 312:643–646 (13 Dec. 1984). The DNA encoding the MSP extracellular domain is cleaved by a restriction enzyme at or proximal to the 3' end of the DNA encoding the domain and at a point at or near the DNA encoding the N-terminal end of the mature MSP polypeptide (where use of a different leader is contemplated) or at or proximal to the N-terminal coding region for the MSP (where the native MSP signal is employed). This DNA fragment then is readily inserted into DNA encoding e.g. an immunoglobulin light or heavy chain constant region and, if necessary, tailored by deletional mutagenesis. Preferably, this is a human immunoglobulin. DNA encoding immunoglobulin light or heavy chain constant regions is known or readily available from cDNA libraries or is synthesized. See for example, Adams et al., Biochemistry 19:2711–2719 (1980); Gough et al., Biochemistry 19:2702–2710 (1980); Dolby et al., P.N.A.S. USA, 77:6027–6031 (1980); Rice et al., P.N.A.S. USA 79:7862–7865 (1982); Falkner et al., Nature 298:286–288 (1982) and Morrison et al., Ann. Rev. Immuno 2:239–256 (1984).

DNA encoding the chimeric chain(s) is transfected into a host cell for expression. If the host cell is producing an immunoglobulin prior to transfection then one need only transfect with the MSP fused to light or to heavy chain to produce a heteroantibody. The aforementioned immunoglobulins having one or more arms bearing the MSP domain and one or more arms bearing companion variable regions result in dual specificity for MSP ligand and for an antigen. These are produced by the above-described recombinant methods or by in vitro procedures. In the latter case, for example, F(ab')$_2$ fragments of the MSP fusion and an immunoglobulin are prepared, the F(ab')2 fragments converted to Fab' fragments by reduction under mild reducing conditions, and then reoxidized in each other's presence under acidic conditions in accord with methods known per se. See also U.S. Pat. No. 4,444,878.

Additionally, procedures are known for producing intact heteroantibodies from immunoglobulins having different specificities. These procedures are adopted for the in vitro production of heterochimeric antibodies by simply substituting the MSP fusions for one of the previously employed immunoglobulins.

In an alternative method for producing a heterofunctional antibody, host cells producing an MSP-immunoglobulin fusion, e.g. transfected myelomas, also are fused with B cells or hybridomas which secrete antibody having the desired companion specificity for an antigen. Heterobifunctional antibody is recovered from the culture medium of such hybridomas, and thus may be produced somewhat more conveniently than by conventional in vitro resorting methods (EP 68,763).

Another class of MSP variants are deletional variants. Deletions are characterized by the removal of one or more amino acid residues from an MSP sequence. Typically, the membrane anchor and cytoplasmic domains of all MSP subunits are deleted. However, any other suitable site N-terminal to the transmembrane which preserves the matrix protein or ligand-binding capability of the MSP is suitable. Excluded from the scope of deletional variants are the protein digestion fragments that may have heretofore been obtained in the course of elucidating amino acid sequences of MSPs.

Substitutional variants are those in which at least one residue in the MSP sequence has been removed and a different residue inserted in its place. Table 1 below describes substitutions which in general will result in fine modulation of the characteristics of an MSP.

TABLE 1

| Original Residue | Exemplary Substitutions |
|---|---|
| Ala | ser |
| Arg | lys |
| Asn | gln; his |
| Asp | glu |
| Cys | ser; ala |
| Gln | asn |
| Glu | asp |
| Gly | pro |
| His | asn; gln |

TABLE 1-continued

| Original Residue | Exemplary Substitutions |
|---|---|
| Ile | leu; val |
| Leu | ile; val |
| Lys | arg; gln; glu |
| Met | leu; ile |
| Phe | met; leu; tyr |
| Ser | thr |
| Thr | ser |
| Trp | tyr |
| Tyr | trp; phe |
| Val | ile; leu |

Substantial changes in function or immunological identity are made by selecting substitutions that are less conservative than those in Table 2, i.e., selecting residues that differ more significantly in their effect on maintaining (a) the structure of the polypeptide backbone in the area of the substitution, for example as a sheet or helical conformation, (b) the charge or hydrophobicity of the molecule at the target site or (c) the bulk of the side chain. The substitutions which in general are expected to produce the greatest changes in MSP properties will be those in which (a) a hydrophilic residue, e.g. seryl or threonyl, is substituted for (or by) a hydrophobic residue, e.g. leucyl, isoleucyl, phenylalanyl, valyl or alanyl; (b) a cysteinyl or prolyl is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanyl, is substituted for (or by) one not having a side chain, e.g., glycyl.

A preferred class of substitutional or deletional variants are those involving a membrane anchor region of the MSP. Transmembrane regions of MSP subunits are highly hydrophobic or lipophilic domains that are the proper size to span the lipid bilayer of the cellular membrane. They are believed to anchor the MSP in the cell membrane. Other cell surface molecules are anchored by lipid modification, as by phospholipid anchors.

Deletion or substitution of the membrane anchor domain will facilitate recovery and provide a soluble form of the MSP by reducing its cellular or membrane lipid affinity and improving its water solubility. If the membrane anchor domains are deleted one avoids the introduction of potentially immunogenic epitopes, either by exposure of otherwise intracellular polypeptides that might be recognized by the body as foreign or by insertion of heterologous polypeptides that are potentially immunogenic. A principal advantage of the membrane anchor domain-deleted MSP is that it is secreted into the culture medium of recombinant hosts. This variant is soluble in body fluids such as blood and does not have an appreciable affinity for cell membrane lipids, thus considerably simplifying its recovery from recombinant cell culture. Surprisingly, MSPs in which membrane inserted chains have been modified so as to be no longer capable of stable insertion into cell membranes are capable of proper association and secretion from recombinant host cells even if the MSP chains are not fused to a multimer-forming sequence such as an immunoglobulin. A multimer-forming sequence is a multichain polypeptide that contains that portion of a multiple chain polypeptide that, when in the unfused form in nature, forms covalently or noncovalently associated multiple chain structures.

It will be amply apparent from the foregoing discussion that substitutions, deletions, insertions or any combination thereof are introduced to arrive at a final construct. None of the variants will have a functional membrane anchor domain and preferably will not have a functional cytoplasmic sequence. This is generally accomplished by deletion of the relevant domain although adequate insertional or substitutional variants also are effective for this purpose. For example, the transmembrane domain is substituted by any amino acid sequence, e.g. a random or predetermined sequence of about 5 to 50 serine, threonine, lysine, arginine, glutamine, aspartic acid and like hydrophilic residues, which altogether exhibit a hydrophilic hydropathy profile. Like the deletional (truncated) MSPs, these variants are secreted into the culture medium of recombinant hosts.

MSP variants are prepared conveniently by site specific mutagenesis of nucleotides in the DNA encoding the MSP, thereby producing DNA encoding the variant, and thereafter expressing the DNA in recombinant cell culture. Obviously, changes in the DNA encoding the variant MSPs must not place the sequence out of reading frame and preferably will not create complementary regions that could produce secondary mPaA structure deleterious to expression (EP 75,444A). The MSP variants typically exhibit the same matrix or ligand binding activity as does the naturally-occurring prototype, although variants also are selected in order to modify the characteristics of the MSP as indicated above.

While the site for introducing an amino acid sequence variation is predetermined, the mutation per se need not be predetermined. For example, in order to optimize the performance of a mutation at a given site, random or saturation mutagenesis (where all 20 possible residues are inserted) may be conducted at the target codon or region and the expressed MSP variants screened for the optimal combination of desired activities.

MSP variants that are not capable of binding to their matrix proteins or ligands are useful nonetheless as immunogens for raising antibodies to the MSP or as immunoassay kit components (labelled, as a competitive reagent for native MSP, or unlabelled as a standard for an MSP assay) so long as at least one MSP epitope remains active.

Contemplated herein are MSPs or MSP amino acid sequence or glycosylation variants (including those already described above) wherein one or more MSP subunits are conjugated with a nonproteinaceous polymer. It will be understood that the nonproteinaceous polymer which is conjugated to MSP excludes oligosaccharides that are present in the same positions in the native or starting MSP, i.e. the polymer is extraneous or heterologous to the MSP.

It is within the scope hereof to move, add or delete glycosylation sites by site-directed mutagenesis of MSP polypeptide in order to increase the number of or change the location of the carbohydrate substituents. The nature of the carbohydrate is modified in conventional fashion by in vitro enzymatic digestion or by selecting host cells that affix the selected carbohydrate (or do not glycosylate at all).

The nonproteinaceous polymer ordinarily is a hydrophilic synthetic polymer, i.e., a polymer not otherwise found in nature. However, polymers which exist in nature and are produced by recombinant or methods are useful, as are polymers which are isolated from nature. Hydrophilic polyvinyl polymers fall within the scope of this invention, e.g. polyvinylalcohol and polyvinylpyrrolidone. Particularly useful are polyalkylene ethers such as polyethylene glycol, polypropylene glycol, polyoxyethylene esters or methoxypolyethylene glycol; polyoxyalkylenes such as polyoryethylene, polyoxypropylene, and block copolymers of polyoxyethylene and polyoxypropylene (Pluronics); polymethacrylates; carbomers; branched or unbranched polysaccharides which comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextran sulfate, dextran, dextrins, glycogen, or the polysaccharide subunit of acid mucopolysaccharides, e.g. hyaluronic acid; polymers of sugar alcohols such as polysorbitol and polymannitol; and heparin. There the polysaccharide is the native glycosylation or the glycosylation attendant on recombinant expression of MSP, the site of substitution ordinarily is located at other than an N or O-linked glycosylation site of the MSP or the MSP variant is an amino acid sequence variant in which an additional or substitute N or O-linked site has been introduced into the molecule.

Mixtures of such polymers are employed, or the polymer may be homogeneous. The polymer prior to crosslinking need not be, but preferably is, water soluble, but the final conjugate must be soluble in biological fluids such as blood. In addition, for therapeutic uses the polymer should not be highly immunogenic when conjugated to the MSP, nor should it possess viscosity that is incompatible with intravenous infusion or injection if it is intended to be administered by such routes.

Preferably the polymer contains only a single group which is reactive with MSP. This helps to avoid crosslinking of MSP molecules. However, it is within the scope herein to optimize reaction conditions to reduce crosslinking, or to purify the reaction products through gel filtration or chromatographic sieves to recover substantially homogeneous derivatives.

The molecular weight of the polymer ranges about from 100 to 500,000, and preferably is about from 1,000 to 20,000. The molecular weight chosen will depend upon the nature of the polymer and the degree of substitution. In general, the greater the hydrophilicity of the polymer and the greater the degree of substitution, the lower the molecular weight that can be employed. Optimal molecular weights will be determined by routine experimentation. Ordinarily, the molecular weight of the MSP-polymer conjugate will exceed about 70,000 although molecules having lesser molecular weights are suitable.

The polymer generally is covalently linked to MSP through a multifunctional crosslinking agent which reacts with the polymer and one or more amino acid or sugar residues of MSP. However, it is within the scope of this invention to directly crosslink the polymer to the MSP by reacting a derivatized polymer with MSP, or vice versa.

A suitable MSP covalent crosslinking site is the N-terminal amino group and epsilon amino groups found on lysine residues, although other amino, imino, carboxyl, sulfhydryl, hydroxyl or other hydrophilic groups serve as useful sites of substitution. The polymer may be covalently bonded directly to MSP without the use of a multifunctional (ordinarily bifunctional) crosslinking agent. Examples of such crosslinking agents include 1,1-bis(diazoacetyl)-2-phenylethane, glutaraldehyde, N-hydroxysuccinimide esters, for example esters with 4-azidosalicylic acid, homobifunctional imidoesters including disuccinimidyl esters such as 3,3'-dithiobis (succinimidyl-propionate), and bifunctional maleimides such as bis-N-maleimido-1,8-octane. Derivatizing agents such as methyl-3-[(p-azido-phenyl) dithio] proptoimidate yield photoactivatable intermediates which are capable of forming cross-links in the presence of light. Alternatively, reactive water soluble matrices such as cyanogen bromide activated carbohydrates and the systems described in U.S. Pat. Nos.3,959,080; 3,969,287; 3,691,016; 4,195,128; 4,247,642; 4,229,537; 4,055,635 and 4,330,440 are suitably modified for cross-linking the polymer and MSP. Covalent bonding to MSP amino groups is accomplished by known chemistries based upon cyanuric chloride, carbonyl diimidazole, aldehyde reactive groups (PEG alkoxide plus diethyl acetal of bromoacetaldehyde; PEG plus DMSO and acetic anhydride, or PEG chloride plus the phenoxide of 4-hydroxybenzaldehyde, succinimidyl active esters, activated dithiocarbonate PEG, 2,4,5-trichlorophenylchloroformate or p-nitrophenylchloroformate activated PEG. Carboxyl groups are derivatized by coupling PEG-amine using carbodiimide.

Polymers are conjugated to the oligosaccharide substituents by chemical, e.g. metaperiodate, or enzymatic oxidation, e.g. glucose or galactose oxidase, (to produce the aldehyde derivative of the carbohydrate), followed by reaction with hydrazide or amino-derivatized polymers, in the same fashion as is described by Heitzmann et al., P.N.A.S., 71:3537–3541 (1974) or Bayer et al., Methods in Enzymology, 62:310 (1979), for the labeling of oligosaccharides with biotin or avidin. Further, other chemical or enzymatic methods which have been used heretofore to link oligosaccharides and polymers may be suitable. Substituted oligosaccharides are particularly advantageous since there are fewer carbohydrate substitutions than amino acid sites for derivatization, thus improving the stability, activity and homogeneity of the conjugate. Finally, the MSP oligosaccharide substituents are enzymatically modified to remove sugars, e.g. by neuraminidase digestion, as a final product or prior to polymer derivatization.

The polymer will bear a group which is directly reactive with an amino acid side chain, or the N- or C- terminus of MSP, or which is reactive with the multifunctional cross-linking agent. In general, polymers bearing such reactive groups are known for the preparation of immobilized proteins. In order to use such chemistries here, one should employ a water soluble polymer otherwise derivatized in the same fashion as insoluble polymers heretofore employed for protein immobilization. Cyanogen bromide activation is a particularly useful procedure to employ in crosslinking polysaccharides to MSP.

"Water soluble" in reference to the starting polymer means that the polymer or its reactive intermediate used for conjugation is sufficiently water soluble to participate in a derivatization reaction with MSP.

The degree of substitution of MSP will vary depending upon the number of reactive sites on the protein, whether intact or truncated MSP is used, whether the MSP is a fusion with a protein heterologous to MSP, the molecular weight, hydrophilicity and other characteristics of the polymer, and the particular sites chosen. In general, the MSP portion of the conjugate is substituted with about from 1 to 10 polymer molecules, while any heterologous sequence which is fused to MSP may be substituted with an essentially unlimited number of polymer molecules so long as the activity of the MSP moiety is not significantly adversely affected. The optimal degree of crosslinking is easily determined by an experimental matrix in which the time, temperature and other reaction conditions are varied to change the degree of substitution, after which the ability of the conjugates to bind matrix protein or ligand is determined.

The polymer, e.g., PEG is crosslinked to MSP by a wide variety of methods known per se for the covalent modification of proteins with nonproteinaceous polymers such as PEG. Certain of these methods, however, are not preferred for the purposes herein. Cyanuric chloride chemistry leads to many side reactions, including protein cross-linking. In addition, it may be particularly likely to lead to inactivation of proteins containing sulfhydryl groups. Carbonyl diimidazole chemistry (Beauchamp et al., "Anal. Biochem." 131:25–33 [1983]) requires high pH (>8.5), which can inactivate proteins. Moreover, since the "activated PEG" intermediate can react with water, a very large molar excess of "activated PEG" over protein is required. In general, aldehyde chemistry (Royer, U.S. Pat. No. 4,002,531) is preferred since it requires only a 40 fold molar excess of PEG and a 1–2 hr incubation. However, the manganese dioxide suggested by Royer for preparation of the PEG aldehyde is problematic "because of the pronounced tendency of PEG to form complexes with metal-based oxidizing agents" (Harris et al., "J. Polym. Sci., Polym. Chem. Ed." 22:341–352 [1984]). Use of a moffatt oxidation, utilizing DMSO and acetic anhydride, obviates this problem. In addition, the sodium borohydride suggested by Royer must be used at a high pH and has a significant tendency to reduce disulphide bonds. In contrast, sodium cyanoborohydride, which is effective at neutral pH, has very little tendency to reduce disulphide bonds.

The MSP conjugates of this invention typically are separated from unreacted starting materials by gel filtration. Most conveniently, MSP conjugates are eluted from hydrophobic interaction chromatography medium, e.g. alkyl Sepharose, by the use of a decreasing salt gradient. This, as well as the gel filtration approach described above, resolves conjugates on the basis of the degree of substitution.

The DNA encoding an MSP is obtained by known procedures, in most instances by reference to publications describing DNA encoding the MSP. In general, prokaryotes are used for cloning of MSP variant DNA sequences. For example, a λ-resistant strain of $E.\ coli$ JM 101 for propagating M13 phage; Messing et al., Nucl. Acids. Res. 9(2):309–321 [1981]); and $E.\ coli$ K12 strain 294 (ATCC No. 31446) are particularly useful. Other microbial strains which may be used include $E.\ coli$ B, or UM101. These examples are illustrative rather than limiting. Nucleic acid also is cloned using various well known in vitro amplification processes.

DNA encoding the variant MSPs are inserted for expression into vectors containing promoters and control sequences which are derived from species compatible with the intended host cell. The vector ordinarily, but need not, carry a replication site as well as one or more marker sequences which are capable of providing phenotypic selection in transformed cells. For example, $E.\ coli$ is typically transformed using a derivative of pBR322which is a plasmid derived from an $E.\ coli$ species (Bolivar, et al., Gene 2:95 [1977]). pBR322 contains genes for ampicillin and tetracycline resistance and thus provides easy means for identifying transformed cells. The pBR322 plasmid, or other microbial plasmid must also contain or be modified to contain promoters and other control elements commonly used in recombinant DNA constructions.

Promoters suitable for use with prokaryotic hosts illustratively include the β-lactamase and lactose promoter systems (Chang et al., Nature, 275:615 [1978]; and Goeddel et al., Nature 281:544 [1979]), alkaline phosphatase, the tryptophan (trp) promoter system (Goeddel, Nucleic Acids Res. 8:4057 [1980] and EPO Appln. Publ. No. 36,776) and hybrid promoters such as the tac promoter (H. de Boer et al., Proc. Natl. Acad. Sci. USA 80:21–25 [1983]). However, other functional bacterial promoters are suitable. Their nucleotide sequences are generally known, thereby enabling a skilled worker operably to ligate them to DNA encoding the MSP variant using linkers or adaptors to supply any required restriction sites (Siebenlist et al., Cell 20:269 [1980]). Promoters for use in bacterial systems also will contain a Shine-Dalgarno (S.D.) sequence operably linked to the DNA encoding the antigen.

In addition to prokaryotes, eukaryotic microbes such as yeast cultures also are useful as cloning or expression hosts. *Saccharomyces cerevisiae*, or common baker's yeast is the most commonly used eukaryotic microorganism, although a number of other strains are commonly available. For expression in Saccharomyces, the plasmid YRp7, for example, (Stinchcomb, et al., Nature 282:39 [1979]; Kingsman et al, Gene 7:141 [1979]; Tschemper et al., Gene 10:157 [1980]) is commonly used. This plasmid already contains the trpl gene which provides a selection marker for a mutant strain of yeast lacking the ability to grow in tryptophan, for example ATCC no. 44076 or PEP4-1 (Jones, Genetics 85:12 [1977]). The presence of the trpl lesion as a characteristic of the yeast host cell genome then provides an effective means of selection by growth in the absence of tryptophan.

Suitable promoting sequences for use with yeast hosts include the promoters for 3-phosphoglycerate kinase (Hitzeman et al., J. Biol. Chem. 255:2073 [1980]) or other glycolytic enzymes (Hess et al., J. Adv. Enzyme Reg. 7:149 [1968]; and Holland, Biochemistry 17:4900 [1978]), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephospbate isomerase, phosphoglucose isomerase, and glucokinase.

Other yeast promoters, which are inducible promoters having the additional advantage of transcription controlled by growth conditions, are the promoter regions for alcohol dehydrogenase 2, isocytochrome C, acid phosphatase, degradative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in R. Hitzeman et al., European Patent Publication No. 73,657A. Yeast enhancers also are advantageously used with yeast promoters.

Promoters for controlling transcription from vectors in mammalian host cells may be obtained from various sources, for example, the genomes of viruses such as polyoma, Simian Virus 40 (SV40), adenovirus, retroviruses, hepatitis-B virus and most preferably cytomegalovirus, or from heterologous mammalian promoters, e.g. the beta actin promoter. The early and late promoters of the SV40 virus are conveniently obtained as an SV40 restriction fragment which also contains the SV40 viral origin of replication. Fiers et al., Nature, 273:113 (1978). The immediate early promoter of the human cytomegalovirus is conveniently obtained as a HindIII E restriction fragment. Greenaway, P. J. et al., Gene 18:355–360 (1982). Of course, promoters from the host cell or related species also are useful.

DNA transcription in higher eukaryotes is increased by inserting an enhancer sequence into the vector. Enhancers are cis-acting elements of DNA, usually from about 10 to 300 bp, that act to increase the transcription initiation capability of a promoter. Enhancers are relatively orientation and position independent having been found 5' (Laimins, L. et al., Proc.Natl.Acad.Sci. 78:993 [1981]) and 3' (Lusky, M. L., et al., Mol. Cell Bio. 3:1108 [1983]) to the transcription unit, within an intron (Banerji, J. L. et al., Cell 33:729 [1983]) as well as within the coding sequence itself (Osborne, T. F., et al., Mol. Cell Bio 4:1293 [1984]). Many enhancer sequences are now known from mammalian genes (globin, elastase, albumin, α-fetoprotein and insulin). Typically, however, one will use an enhancer from a eukaryotic cell virus. Examples include the SV40 enhancer on the late side of the replication origin (bp 100–270), the cytomegalovirus early promoter enhancer, the polyoma enhancer on the late side of the replication origin, and adenovirus enhancers.

Expression vectors used in eukaryotic host cells (yeast, fungi, insect, plant, animal, human or nucleated cells) may also contain sequences necessary for the termination of transcription which may affect mRNA expression. These regions are transcribed as polyadenylated segments in the untranslated portion of the mRNA encoding the MSP.

Expression vector systems generally will contain a selection gene, also termed a selectable marker. Examples of suitable selectable markers for mammalian cells are dihydrofolate reductase (DHFR), thymidine kinase or neomycin. When such selectable markers are successfully transferred into a mammalian host cell, the transformed mammalian host cell can survive if placed under selective pressure. There are two widely used distinct categories of selective regimes. The first category is based on a cell's metabolism and the use of a mutant cell line which lacks the ability to grow independent of a supplemented medium. Two examples are: CRO DHFR⁻ cells and mouse LTK⁻ cells. These cells lack the ability to grow without the addition of such nutrients as thymidine or hypoxanthine. Because these cells lack certain genes necessary for a complete nucleotide synthesis pathway, they cannot survive unless the missing nucleotides are provided in a supplemented medium. An alternative to supplementing the medium is to introduce an intact DHFR or TK gene into cells lacking the respective genes, thus altering their growth requirements. Individual cells which were not transformed with the DHFR or TK gene will not be capable of survival in non supplemented media.

The second category is dominant selection which refers to a selection scheme used in any cell type and does not require the use of a mutant cell line. These schemes typically use a drug to arrest growth of a host cell. Those cells which have a novel gene would express a protein conveying drug resistance and would survive the selection. Examples of such dominant selection use the drugs neomycin, Southern P. and Berg, P., J. Molec. Appl. Genet. 1:327 (1982), mycophenolic acid, Mulligan, R. C. and Berg, P. Science 209:1422 (1980) or hygromycin, Sugden, B. et al., Mol. Cell. Biol. 5:410–413 (1985). The three examples given above employ bacterial genes under eukaryotic control to convey resistance to the appropriate drug G418 or neomycin (geneticin), xgpt (mycophenolic acid) or hygromycin, respectively.

"Amplification" refers to the increase or replication of an isolated region within a cell's chromosomal DNA. Amplification is achieved using a selection agent e.g. methotrexate (MTX) which is inactivated by DHFR. Amplification or the making of successive copies of the DHFR gene results in greater amounts of DHFR being produced in the face of greater amounts of MTX. Amplification pressure is applied notwithstanding the presence of endogenous DHFR, by adding ever greater amounts of MTX to the media. Amplification of a desired gene can be achieved by cotransfecting a mammalian host cell with a plasmid having a DNA encoding a desired protein and the DHFR or amplification gene permitting cointegration. One ensures that the cell requires more DHFR, which requirement is met by replication of the selection gene, by selecting only for cells that can grow in the presence of ever-greater MTX concentration. So long as the gene encoding a desired heterologous protein has cointegrated with the selection gene replication of this gene gives rise to replication of the gene encoding the desired protein. The result is that increased copies of the gene, i.e. an amplified gene, encoding the desired heterologous protein express more of the desired heterologous protein.

Preferred host cells for expressing the MSP variants of this invention are mammalian host-vector systems, examples of suitable hosts including: monkey kidney CV1 line transformed by SV40 (COS-7, ATCC CRL 1651); human embryonic kidney line (293, Graham, F. L. et al., J. Gen Virol. 36:59 [1977] and 293S cells, either of which are equally satisfactory); baby hamster kidney cells (BHK, ATCC CCL 10); chinese hamster ovary-cells DHFR (CHO, Urlaub and Chasin, Proc.Natl.Acad.Sci. (USA) 77:4216, [1980]); mouse sertoli cells (TM4, Mather, J. P., Biol. Reprod. 23:243–251 [1980]); monkey kidney cells (CV1 ATCC CCL 70); african green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G02, HB 8065); mouse mammary tumor (MMT 060562, ATCC CCL51 cells); and TRI cells (Mather, J. P. et al., Annals N.Y. Acad. Sci. 383:44–68 [1982]).

"Transformation" means introducing DNA into an organism so that the DNA is replicable, either as an extrachromosomal element or by chromosomal integration. One suitable for transformation of the host cells is the method of Graham, F. and van der Eb, A., Virology 52:456–457 (1973). However, other methods for introducing DNA into cells such as by nuclear injection or by protoplast fusion may also be used. If prokaryotic cells or cells which contain substantial cell walls are used as hosts, the preferred method of transfection is calcium treatment using calcium chloride as described by Cohen, F. N. et al., Proc. Natl. Acad. Sci. (USA), 69:2110 (1972).

Construction of suitable vectors containing the desired coding and control sequences employ standard and manipulative ligation techniques. Isolated plasmids or DNA fragments are cleaved, tailored, and religated in the form desired to form the plasmids required. Suitable procedures are well known for the construction described herein. See, for example, (Maniatis, T. et al., *Molecular Cloning*, 133–134 Cold Spring Harbor, [1982]; "Current Protocols in Molecular Biology", edited by Ausubel et al., [1987], pub. by Greene Publishing Associates & Wiley-Interscience).

Ordinarily, DNA encoding each subunit of a given MSP (or transmembrane modified variant) is simultaneously cotransfected into the host cell, although such transfections can be done sequentially. MSP variants in which one subunit is exchanged for the analogous subunit of another MSP (to produce heterologous heterodimers) are produced by cotransforming a recombinant host (typically mammalian cell) with each of the heterologous subunits, for example, exchanging the fibronectin α subunit for the α subunit of GPIIb-IIIa (an α subunit exchange), or the fibronectin β subunit for the β subunit of GPIIb-IIIa (a β subunit exchange).

Correct plasmid sequences are confirmed by transforming *E. coli* K12 strain 294 (ATCC 31446) with ligation mixtures, successful transformants selected by ampicillin or tetracycline resistance where appropriate, plasmids from the transformants prepared, and then analyzed by restriction enzyme digestion and/or sequenced by the method of Messing et al., Nucleic Acids Res. 9:309 (1981) or by the method of Maxam et al., Methods in Enzymology 65:499 (1980).

Host cells are transformed with the expression vectors of this invention. Thereafter they are cultured in appropriate culture media, e.g. containing substances for inducing promoters, selecting transformants or amplifying genes. The culture conditions, such as temperature, pH and the like, are those previously used with the host cell selected for expression, and will be apparent to the ordinarily skilled artisan. For expression of GPIIb-IIIa it is preferable that the culture medium contain calcium and magnesium salts since divalent cations are needed to enhance the stability of secreted GPIIb-IIIa and other calcium dependent MSPs.

The secreted MSP variants are recovered and purified from the culture supernatants or lysates of recombinant hosts. Typically, the supernatants are concentrated by ultrafiltration, contacted with a ligand (e.g. RGD) or matrix protein affinity or immunoaffinity resin so as to adsorb the MSP variant, and eluted from the adsorbent. Optionally, the MSP is purified by HPLC, lectin columns, gel exclusion, hydrophobic interaction or ion exchange chromatography.

The purified MSP is formulated into conventional pharmacologically acceptable excipients.

The soluble MSP variants of this invention are useful in therapeutics, diagnostics and preparative procedures. In diagnostics, the soluble MSPs are employed in place of membrane extracts as standards or controls, or are labelled with a radioisotope or other detectable group for use in competitive-type radioimmuno- or radioreceptor assays for the MSP or its antibodies.

The soluble MSPs are crosslinked to insoluble supports by the methods described herein and employed for the purification of their ligands or matrix proteins, e.g. fibronectin, fibrinogen and the like. Alternatively, the soluble MSPs are used to adsorb ligand or matrix protein in solution, followed by precipitation by antisera, ammonium sulfate or the like in order to recover the ligand or matrix protein complex. The complex is then dissociated by HPLC, electrophoresis, gel chromatography or other conventional methods.

Therapeutic uses of soluble MSPs will be a function of the biological activity of each MSP, and will be apparent therefrom. The soluble MSP variants herein may act as agonists or antagonists of the corresponding native, membrane-bound receptors. The soluble GPIIb-IIIa receptor, for example, is useful as an anticoagulant and for the treatment of disorders associated with platelet aggregation, particularly in the prevention of reocclusion following thrombolytic therapy. Soluble matrix receptors, especially soluble GPIIb-IIIa, also are useful as antagonists to matrix-adhesion dependent neoplastic metastasis. Soluble LFA-1 variants are an antagonist of T-lymphocyte function, thereby being efficacious as immunosuppressive or anti-inflammatory agents, particularly in reperfusion injury. Soluble Mac-1 variants may find use in the treatment of complement activation disorders.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 μg of plasmid or DNA fragment is used with about 2 units of enzyme in about 20 μl of buffer solution. For the purpose of isolating DNA fragments for plasmid construction, typically 5 to 50 μg of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide or agarose gel to isolate the desired fragment.

"Recovery" or "isolation" of a given fragment of DNA from a restriction digest means separation of the digest on polyacrylamide or agarose gel by electrophoresis, identification of the fragment of interest by comparison of its mobility versus that of marker DNA fragments of known molecular weight, removal of the gel section containing the desired fragment, and separation of the gel from DNA. This procedure is known generally (Lawn, R. et al., Nucleic Acids Res. 9:6103–6114 [1981], and Goeddel, D. et al., Nucleic Acids Res. 8:4057 [1980]).

"Ligation" refers to the process of forming phosphodiester bonds between two double stranded nucleic acid fragments (Maniatis, T. et al., Id. at 146). Unless otherwise provided, ligation may be accomplished using known buffers and conditions with 10 units of T4 DNA ligase ("ligase") per 0.5 μg of approximately equimolar amounts of the DNA fragments to be ligated.

The following examples merely illustrate the best mode now contemplated for practicing the invention, but should not be construed to limit the invention. All literature citations herein are expressly incorporated by reference.

EXAMPLE 1

Cloning of Glycoprotein IIb (GPIIb) cDNA

Messenger RNA was prepared from cultured human erythroleukemia cells (HEL, ATCC TIB 180). An oligo(dT)-primed cDNA library was prepared using this mRNA in the bacteriophage lambda ZAP (Stratagene Cloning Systems). The lambda ZAP library was screened with a 45-mer oligonucleotide (2bl) derived from the 5' end of the published cDNA sequence for GPIIb from HEL cells (Poncz et al., "J. Biol. Chem." 262(18):8476–8482 [1987]). Several positively-hybridizing phage were purified, and the cDNA inserts they contained were subjected to restriction enzyme digestion analysis. From these results a phage which appeared to contain a full-length coding insert for GPIIb was selected for further analysis. DNA sequencing of this phage insert DNA gave over 300 bases which corresponded exactly with the published cDNA sequence from the 5' end of the mRNA (Poncz et al.) except having 4 additional bases on its 5' end. The cDNA insert was digested with EcoRI (this site being derived from the linkers ligated to the ends of the cDNAs during production of the library) and HindIII, which cuts the GPIIb insert uniquely downstream of the end of the coding sequence. This EcoRI to HindIII restriction fragment, containing the entire coding region for GPIIb was ligated into mammalian cell expression vector pRK5 (U.S. Ser. No. 07/097,472) which had been digested with EcoRI and HindIII, and expression vector CPIIb-pRK5 was recovered.

Construction of Full-Length Glycoprotein IIIa (GPIIIa) cDNA

A cDNA clone for GPIIIa, incomplete at its 5' end, was obtained (Rosa et al., "Blood" 72(2):593 [1988]). The cDNA was provided as an EcoRI (site derived from the cDNA library construction linker) to PstI (site downstream of the end of the coding sequence) insert in the plasmid vector pIBI20 (International Biotechnologies, Inc.) This plasmid was digested with HindIII to cut the plasmid at the unique HindIII site in pIBI20 downstream of the terminal PstI site in the cDNA insert, and incompletely with ApaI, to give a cDNA fragment bounded by the ApaI site at the 5' end of the sequence and HindIII from the plasmid vector. The relevant domain for the construction is shown below.

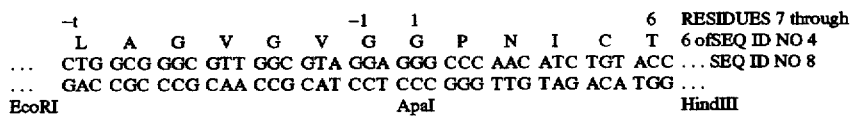

```
       -4                        -1  1                    6    RESIDUES 7 through
        L    A    G    V    G    V   G    P    N    I    C    T    6 of SEQ ID NO 4
   ... CTG  GCG  GGC  GTT  GGC  GTA GGA  GGG  CCC  AAC  ATC  TGT  ACC ... SEQ ID NO 8
   ... GAC  CGC  CCG  CAA  CCG  CAT CCT  CCC  GGG  TTG  TAG  ACA  TGG ...
     EcoRI                          ApaI                            HindIII
```

Synthetic complementary oligonucleotides were used to reconstruct a full-length coding construct for GPIIIa based on the published cloned cDNA sequence (Fitzgerald et al., "J. Biol. Chem." 262(9):3936 [1987]). The oligonucleotide sequence, ending in ApaI, was ligated to the ApaI site of the above ApaI-HindIII fragment, to give a DNA fragment now bounded by EcoRI and HindIII. This EcoRI to HindIII fragment, containing the entire coding region for GPIIIa was ligated into pRK5 which had been digested with EcoRI and HindIII, and expression vector GPIIIa-pRK5 was recovered. The relevant oligonucleotide sequences are shown below.

```
              -26
               M   R   A   R   P   R   P   R   P   L   W
        AAT TCT AGA GCC GCC ATG AGA GCA CGT CCT CGA CCA CGT CCT CTC TGG -
              GA TCT CGG CGG TAC TCT CGT GCA GGA GCT GGT GCA GGA GAG ACC -
        EcoRI
          XbaI
                                                                        RESIDUES 26
                                                                    -1    1    through 2 of
         A   T   V   L   A   L   G   A   L   A   G   V   G   V   G   G   P  SEQ ID NO 4
        GCG ACT GTG CTG GCA CTG GGA GCA CTC GCT GGT GTT GGA GTA GGA GGG CC SEQ ID NO 9
        CGC TGA CAC GAC CGT GAC CCT CGT GAC CGA CCA CAA CCT CAT CCT C
                                                                       ApaI SEQ ID NO 10
```

Figure 3:
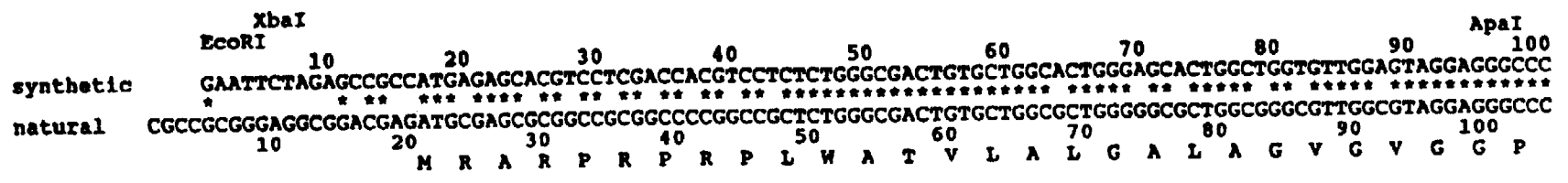

The synthetic oligonucleotides were designed such that the amino acids encoded were identical to those predicted from the published cloned cDNAs (Fitzgerald et al., Rosa et al.), but the codons were not always identical with the naturally-occurring cloned cDNA. FIG. 3 compares the coding strands of the synthetic and natural sequences. Asterisks between each sequence indicate which nucleotides are identical. These changes were introduced for three reasons.

1. In light of difficulties encountered in sequencing the cDNA, we concluded that the cDNA could contain secondary structure adverse to translational efficiency. To minimize possible secondary structure in the mRNA produced from expression constructs, the percentage of G and C bases in the natural coding sequence was lessened by changing some codons to others which had a lower G and/or C content, but which coded for the same amino acid. These altered codons were chosen such that only codons used frequently in the remainder of the cDNA were substituted. Karnick et al., "J. Biol. Chem. 262(5):9255 (1987); Devlin et al., "Gene" 65:13 (1988).

2. The codon for arginine (R, amino acid-25), immediately following the initiator methionine codon (M -26), was changed from CGA to AGA. Kozak, "Nucl. Acids Res." 15(20):8125 [1987] and Kozak, "J. Mol. Biol." 196:947 [1987].

3. The DNA sequence upstream of the initiator methionine codon was not based on the natural DNA sequence. The synthetic complementary oligonucleotides were such that an EcoRI site was present at one end, followed by an XbaI recognition sequence, and then followed by a GCC GCC motif immediately upstream of the initiator methionine. Kozak, "J. Mol. Biol." Id.

The plasmids encoding GPIIb and GPIIIa (GPIIb-pRK5 and GPIIIa-pRK5) were transletted in 293S cells and cultured under conventional conditions for transient expression as described below. The cells were harvested and analyzed for GPIIb-IIIa expression. Expression was confirmed by the presence of correctly sized bands on a Western gel, immunologically visualized by FACS sorting, and immunoprecipitation of intact cells labeled metabolically with $S^{35}$ or by $^{125}I$ surface-labelling.

EXAMPLE 2

Construction of cDNA Encoding Truncated GPIIb

The starting point for the construction of the GPIIb truncated form was the full-length coding construction for GPIIb described in Example 1. The relevant domain for this construction is shown below.

```
                                                 putative transmembrane
                                                      region
                                              962
                L   R   A   L   E   E   R   A   I        SEQ ID NO:11
            ... CTC CGG GCC TTG GAG GAG AGG GCC ATT ... SEQ ID NO:12
            ... GAG GCC CGG AAC CTC CTC TCC CGG TAA ...
           EcoRI                  StyI
```

The DNA fragment from the EcoRI site (upstream of the initiator ATG codon) to the StyI site indicated above was isolated and ligated to complementary synthetic oligonucleotides such that the DNA sequence thus obtained coded for the natural GPIIb sequence up to amino acid residue 962 (arginine) and was then followed by a TGA stop codon.

```
                                      Residues 958 through 962
          A   L   E   E   R  Stop    of SEQ ID NO:2
          C TTG GAG GAG AGG TGA TGA A SEQ ID NO:13
                CTC CTC TCC ACT ACT TTC GA SEQ ID NO:14
           StyI                   HindIII
```

In the natural sequence, arginine 962 is followed by an approximately 26 amino acid putative hydrophobic transmembrane domain and a cytoplasmic domain (Poncz et al.). Thus, in this construction both of these domains have been deleted from the coding region of the construction. The end of the synthetic fragment terminated in a HindIII restriction site. The entire DNA fragment bounded by EcoRI and HindIII restriction sites was ligated into pRK5 which had been digested with EcoRI and HindIII. Expression vector GPIIbtrunc-pRK5 was recovered.

The EcoRI to HindIII fragment outlined above was rescued from GPIIbtrunc-pRK5 and subjected to analysis by DNA sequencing. Over 250 bases from each end of the insert were sequenced and corresponded exactly to that which was predicted.

Construction of cDNA Encoding Truncated GPIIIa

The starting point for the construction of the GPIIIa truncated form was the full-length coding construction for GPIIIa described in Example 1. The relevant domain for this construction is shown below.

```
                    692
    P    K    G    P    D    I    L    L      SEQ ID NO:15
... CCC  AAG  GGC  CCT  GAC  ATC  CTG  GTC... SEQ ID NO:16
... GGG  TTC  CCG  GGA  CTG  TAG  GAC  CAC...
    XbaI                ApaI
```

The DNA fragment from the XbaI site (upstream of the initiator ATG codon) to the ApaI site indicated below was isolated and ligated to complementary synthetic oligonucleotides such that the DNA sequence thus obtained coded for the natural GPIIIa sequence up to amino acid residue 692 (aspartic acid) and was then followed by a TGA stop codon.

```
    G   P   D   Stop
    CT  GAC TGA TGA GAT CTA  SEQ ID NO:17
    CCG GGA CTG ACT ACT CTA TCG A  SEQ ID NO:18
    ApaI                HindIII
```

In the natural sequence, aspartic acid 692 is followed by an approximately 29 amino acid putative hydrophobic transmembrane domain and a cytoplasmic domain (Fitzgerald et. al.) Thus, in this construction both of these domains have been deleted from the coding region of the construction. The end of the synthetic fragment terminated in a HindIII restriction site. The entire fragment bounded by XbaI and HindIII restriction sites, was ligated into pRK5 previously digested with XbaI and HindIII and trunc expression vector GPIIIatrunc-pRK5 was recovered.

The XbaI to HindIII fragment outlined above was rescued from GPIIIatrunc-pRK5, and subjected to analysis by DNA sequencing. Over 200 bases from each end of the insert were sequenced and corresponded exactly to that which was predicted.

Expression of Truncated Human GPIIb-IIIa Receptor in a Eukaryotic Host

Human embryonic kidney cells (293S) were cotransfected with the expression vectors GPIIbtrunc-pRK5 and GPIIIatrunc-pRK5 using CaPO$_4$ (Graham et al., "Virology" 52:456 [1973]) using the host system described in EP 260,148.

Transient Expression

High levels of transient expression were obtained when 293S cells were cotransfected with GPIIbtrunc-pRK5, GPIIIatrunc-pRK5 and adenovirus VA RNA-DNA (U.S. Ser. No. 07/101,712; Akusjarvietal, "Mol. Cell. Biol." 7:549 [1987]) and grown in standard growth media (50% Dulbeccos Modified Eagle Media, 50% F12 mixture, 2 mM L-glutamine and 10% fetal bovine serum). 16 hours after glycerol shock cells were transferred to serum free media (Dulbeccos Modified Eagle Media, 0.1% glucose, 10 µg/ml insulin) and grown for a further 48 hours, at which time cells and culture media were harvested. Conditioned cell culture fluid was centrifuged to remove contaminating cell debris and then quick frozen in dry ice-ethanol and stored at −70° C. until analyzed. Cells were removed from 6 cm plates by suspension in 0.6 ml of 150 mM NaCl, 10 mM Tris (pH 7.5), 1% Triton X-100, 2 mM PMSF, 0.5 µg/ml leupeptin and 2 µg/ml pepstatin A followed by extraction for 30 minutes on ice with vortexing. Cellular debris was removed by centrifugation at 10,000 g and samples stored at −70° C. The soluble GPIIb-IIIa was recovered by Q-Sepharose (fast-flow) chromatography with 10 column volumes of 20 mM MES buffer/1 mM. CaCl$_2$ pH 6.5 and gradient elution over 0–400 mM NaCl. The peak soluble GPIIb-IIIa tended to elute at about 200–250 mM NaCl. The eluate was concentrated to 3% of the column volume of an S-300 column, after which the concentrate was exclusion chromatographed on the a-350 column using 10 mM Tris/150 mM NaCl/1 mM CaCl$_2$ pH 7.5. Some of the full length GPIIb transfected into 293S cells associated with endogenous $\alpha_v$. The secretion of soluble GPIIb with soluble GPIIIa avoided the need to purify BPIIb-IIIa from the $\alpha_v B_3$ vitronectin receptor, as would have been the case if the full length subunits had been used. See Bodary et al., J. Biol. Chem. 32:18859 (Nov. 15, 1989).

Stable Expression

Stable 293S clones expressing truncated GPIIb-IIIa were established by co-transfection of GPIIbtrunc-pRK5 and GPIIIatrunc-pRK5 with pRSVneo (Gorman et al., "Science" 221:551–552 [1983]). Forty eight hours after transfection cells were passaged into standard growth media containing 800 µg/ml of G418. Two weeks later, G418 resistant clones were picked and grown in standard growth media containing 400 µg/ml of G418. Clones were grown for 48 hours in serum free medium and the conditioned culture medium assayed for the expression of secreted forms of GPIIb-IIIa by Western blot analysis.

Analysis of Expressed Truncated GPIIb-IIIa

Transiently transfected cells were assayed for expression by pulse-chase analysis followed by immunoprecipitation using a panel of monoclonal antibodies generated against purified platelet GPIIb-IIIa. S$^{35}$-cysteine and -methionine metabolically labeled proteins were recovered from the culture fluid of cells cotransfected with both GPIIbtrunc-pRK5 and GPIIIatrunc-pRK5 as described above. Truncated GPIIb-IIIa was immunoprecipitated from cell culture fluid with a panel of mouse monoclonal antibodies (AP2 [Montgomery et al., "J. Clin. Invest." 71:385 (1983)], 2D2, 3A8, 4B12, and AP3 [Newman et al., "Blood" 65:227 (1985)]) by incubation with Protein A Sepharose CL4B (Pharmacia), bound to rabbit IgG antibodies directed against mouse IgG. Electrophoresis of the immunoprecipitated proteins demonstrated the secretion of recombinant truncated GPIIb-IIIa whose size was in agreement with the molecular weights expected of the modified cDNAs. Monoclonal antibodies specific to the GPIIb-IIIa complex (AP2), GPIIb (2D2, 3A8) and GPIIIa (4B12, AP3) all immunoprecipitate both the GPIIb and GPIIIa truncated proteins, demonstrating that the recombinant secreted proteins are present in the form of a complex. Cells which received no DNA or the GPIIbtrunc-pRK5 alone or GPIIIatrunc-pRK5 alone do not secrete proteins at levels which are detectable by monoclonal antibodies to GPIIb or GPIIIa.

The expression of individual subunits of GPIIb or GPIIIa in transiently transfected cells was demonstrated using Western blot analysis. Cells were extracted as described above and culture media (recovered as above) were concentrated 2-fold by ultrafiltration and analyzed by electrophoresis on polyacrylamide gels (Laemmli, U.K., "Nature" 227:680–685 [1970]) and by Western Blotting (Towbin et al., Proc.Natl.Acad.Sci.USA 76:4350–4354 [1979]). Mouse monoclonal antibodies specific for GPIIb and GPIIIa were used in this analysis. Horse radish peroxidase-conjugated antibodies directed against the murine monoclonals were used to visualize the individual GPIIbtrunc and GPIIIatrunc proteins in the extracts.

The stable clones expressing the GPIIb-IIIa truncated constructs were shown to secrete the recombinant proteins of the expected sizes using Western blot analysis.

That the GPIIb-IIIa trunc proteins secreted from stable clones were present as a complex was demonstrated by their detection, after direct transfer of culture medium to nitrocellulose by aspiration, with monoclonal antibody AP2.

The truncated GPIIb or GPIIIa proteins were not detected in culture media when expressed as individual subunits: either they are not secreted or the efficiency of secretion is reduced to levels which preclude detection by immunoprecipitation or by Western blot analysis.

EXAMPLE 3

Demonstration of Fibrinogen Binding of Secreted Human GPIIb-IIIa Polypeptide Complex The functional activity of the secreted truncated GPIIb-IIIa is shown by its specific absorption to an affinity matrix containing the natural ligand, fibrinogen, for the GPIIb-IIIa receptor.

A stable clone from Example 2 which was expressing the GPIIb-IIIa truncated polypeptide complex was grown for 20 hours under serum free conditions (DMEM culture medium, 0.1% glucose, 10 µg/ml insulin, 1.5 µg/ml L-cysteine, 2.4 µg/ml L-methtonine, 200 µCi/ml $S^{35}$ methionine and 200 µCi/ml $S^{35}$ cysteine). The conditioned cell culture fluid was first concentrated by ultrafiltration then purified by fibrinogen affinity chromatography. The fibrinogen affinity column was produced by coupling highly purified human fibrinogen to CNBr-activated Sepharose 4B (Pharmacia) using the manufacturer's recommended procedure. The concentrated cell culture fluid was applied first to a control Tris/ethanolamine reacted CNBr-activated Sepharose 4B column and the unbound material applied directly to the fibrinogen-Sepharose column. The contaminating proteins were washed away at room temperature with phosphate buffered saline solution containing 1 mM $Ca^{2+}$, 1 mM $Mg^{2+}$, 25 mM octylglucoside (OG) and 2 mM phenylmethylsulfonylfluoride (PMSF). The bound GPIIb-IIIa was eluted from the column at room temperature with phosphate buffered saline containing 15 mM EDTA, 25mM OG and 2 mM PMSF. The eluted GPIIb-IIIa was hen concentrated by ultrafiltration and the subunits of expected molecular weight identified by autoradiography and by Western blot analysis using monoclonal antibodies specific to GPIIb (3A8) and GPIIIa (4B12). The specificity of the binding to the fibrinogen column is shown by the absence of the protein in the eluate from the control column determined by both methods.

EXAMPLE 4

Expression of LFA-1 and Mac-1 truncations

LFA-1 and Mac-1 are integrins having identical beta chains (beta-2) and distinct alpha chains (alpha L and alpha M, respectively). In this study the full length chains were transformed into host cells. In addition, the DNA encoding the transmembrane domains of the alpha and beta chains of each of these integrins was deleted and the truncated DNAs transformed into host cells for coexpression.

Transformants with full length LFA-1 alphaL chain did not express any detectable cell bound alphaL, but cotranformation with truncated alphaL and truncated beta-2, or with truncated alphaM and truncated beta-2, resulted in the secretion of the truncated heterodimers. Interestingly, transformation with the full length alphaM chain of Mac-1 alone did yield cell surface alphaM. It has not been confirmed that this product represents a stable alphaM monomer since it is conceivable that the recombinant alphaM chain became associated with a beta chain endogenous to the host cell.

We claim:

1. A soluble analogue of a multiple subunit polypeptide (MSP),
- wherein the MSP is an integrin comprising an α and a β subunit, said integrin selected from the group consisting of GPIIb-IIIa; p-150,95; Mac-1; LFA-1; a leukocyte adhesion receptor; a member of the VLA family; and a heterodimeric receptor that participates directly in intercellular adhesion or adhesion of cells to extracellular matrix proteins;
- wherein the soluble analogue comprises two subunit variants and does not comprise an immunoglobulin constant domain,
- wherein the two subunit variants are variants of a native MSP subunit, associate naturally with each other, are encoded by discrete nucleic acids, and lack a functional membrane anchor domain.

2. The analogue of claim 1 which is free of detergent.

3. A sterile aqueous solution comprising the analogue of claim 1.

4. The analogue of claim 1, wherein the membrane anchor domains of the α- and β-subunits of the integrin are deleted.

5. The analogue of claim 4 wherein the cytoplasmic domains of the α- and β-subunits of the integrin are deleted.

6. The soluble analogue of claim 1, wherein the MSP is from a human.

7. A soluble analogue of a multiple subunit polypeptide (MSP),
- wherein the MSP is an integrin comprising an α and a β subunit, said integrin selected from the group consisting of GPIIb-IIIa; p-150,95; Mac-1; LFA-1; a leukocyte adhesion receptor; a member of the VLA family; and a heterodimeric receptor that participates directly in intercellular adhesion or adhesion of cells to extracellular matrix proteins;
- wherein the soluble analogue comprises (1) a first MSP subunit variant fused at its C-terminus to an immunoglobulin constant domain and (2) a second MSP subunit variant which is not fused to an immunoglobulin constant domain,
- wherein the MSP subunit variants associate naturally with each other, are encoded by discrete nucleic acids, and lack a functional membrane anchor domain.

8. The soluble analogue of claim 7 wherein the MSP subunit variants are intermolecularly disulfide bonded to each other.

9. The soluble analogue of claim 7 further comprising an unfused immunoglobulin chain.

10. The soluble analogue of claim 9 wherein the unfused chain is a light chain having its variable domain deleted and the immunoglobulin constant domain is a heavy chain constant domain.

11. The soluble analogue of claim 9 wherein the unfused immunoglobulin chain is an immunoglobulin light chain which comprises a variable domain, and which light chain is disulfide bonded to the immunoglobulin constant domain of the fusion of the immunoglobulin constant domain and the first MSP subunit variant.

12. The soluble analogue of claim 11 further comprising an unfused immunoglobulin heavy chain wherein the unfused immunoglobulin heavy and light chains bind to an antigen.

13. The soluble analogue of claim 7 wherein the transmembrane domain of the first MSP subunit variant is deleted.

14. The soluble analogue of claim 13 wherein the transmembrane domain of the second MSP subunit variant is deleted.

* * * * *